(12) United States Patent
Chatterjee et al.

(10) Patent No.: US 6,310,057 B1
(45) Date of Patent: *Oct. 30, 2001

(54) α-KETOAMIDE MULTICATALYTIC PROTEASE INHIBITORS

(75) Inventors: Sankar Chatterjee, Wynnewood; John P. Mallamo, Glenmoore, both of PA (US)

(73) Assignee: Cephalon, Inc., West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/519,979

(22) Filed: Mar. 7, 2000

Related U.S. Application Data

(62) Division of application No. 09/167,163, filed on Oct. 6, 1998, now Pat. No. 6,096,778.
(60) Provisional application No. 60/061,382, filed on Oct. 7, 1997.

(51) Int. Cl.[7] .................. A61K 31/4015; A61K 31/55; C07D 209/48; C07D 403/12
(52) U.S. Cl. ................ 514/212; 514/417; 514/255; 540/524; 548/477; 544/405
(58) Field of Search .............. 540/524; 548/477; 514/212, 417

(56) References Cited

U.S. PATENT DOCUMENTS

| | | | |
|---|---|---|---|
| 5,034,376 | 7/1991 | Hoover et al. | 514/18 |
| 5,162,500 | 11/1992 | Takeuchi et al. | 530/330 |
| 5,340,825 | 8/1994 | Horwell et al. | 514/339 |
| 5,444,042 | 8/1995 | Bartus et al. | 514/2 |
| 5,514,694 | 5/1996 | Powers et al. | 514/357 |
| 5,550,262 | 8/1996 | Iqbal et al. | 554/57 |
| 5,563,127 | 10/1996 | Amparo et al. | 514/64 |
| 5,610,297 | 3/1997 | Powers | 544/168 |
| 5,614,649 | 3/1997 | Iqbal et al. | 554/56 |
| 5,646,121 | 7/1997 | Häbich et al. | 514/18 |
| 5,650,508 | 7/1997 | Powers | 544/168 |
| 5,658,885 | 8/1997 | Lee et al. | 514/19 |
| 5,698,538 | 12/1997 | Amparo et al. | 514/64 |
| 5,919,765 * | 7/1999 | Marlowe et al. | 514/18 |

FOREIGN PATENT DOCUMENTS

| | | |
|---|---|---|
| 0 604 183 A1 | 6/1994 | (EP) . |
| WO 92/20804 | 11/1992 | (WO) . |
| WO 95/00535 | 1/1995 | (WO) . |
| WO 96/14857 | 5/1996 | (WO) . |
| WO 96/20689 | 7/1996 | (WO) . |
| WO 96/39385 | 12/1996 | (WO) . |

OTHER PUBLICATIONS

Arribas, J. et al., "Autoantibodies Against the Multicatalytic Proteinase in Patients with Systemic Lupus Erythematosus," *J. Exp. Med.*, 1990, 173, 423–427.

Baeuerle, P.A. et al., "Function and Activation of NF–kB in the Immune System," *Annu. Rev. Immunol.*, 1994, 12, 141–179.

Bannister et al., "Aspects of the Structure, Function, and Applications of Superoxide Dismutase," *CRC Crit. Rev. Biochem.*, 1987, 22(2), 111–180.

Beg, A. et al., "An Essential Role for the NF–kB in Preventing TNF–a–Induced Cell Death," *Science*, 1996, 274, 782–784.

Borchelt, D.R. et al., "Superoxide Dismutase 1 With Mutations Linked to Familial Amyotrophic Lateral Sclerosis Possesses Significant Activity," *PNAS*, 1994, 91, 8292–8296.

Bowling, A.C. et al., "Superoxide Dismutase Activity, Oxidative Damage, and Mitochondrial Energy Metabolism in Familial and Sporadic Amyotrophic Lateral Scelerosis," *J. Neurochem.*, 1993, 61, 2322–2325.

Brown, R.H., "Clinical Implications of Basic Research: A Transgenic–Mouse Model of Amyotrophic Lateral Sclerosis," *NEJM*, 1994, 331(16), 1091–1092.

Catzavalos, C. et al., "Decreased Levels of the Cell–Cycle Inhibitor p27kip1 Protein: Prognostic Implications in Primary Breast Cancer," *Nature Med.*, 1997, 3(2), 227–230.

Deng. H.–X.et al., "Amyotrophic Lateral Sclerosis and Structural Defects in Cu, Zn Superoxide Dismutase," *Science*, 1993, 261, 1047–1051.

Drexler, H.C.A., "Activation of the Cell Death Program by Inhibition of Proteasome Function," *PNAS*, 1997, 94, 855–860.

Driscoll, J. et al., "Skeletal Muscle Proteasome Can Degrade Proteins in an ATP–dependent Process that Does Not Require Ubiquitin," *PNAS*, 1989, 86, 787–791.

Fisher, D.E., "Apoptosis in Cancer Therapy Crossing the Threshold," *Cell*, 1994, 78, 539–542.

Fredersdorf, S. et al., "High Level Expression of p27kip1 and Cyclin D1 in Some Human Breast Cancer Cells: Inverse Correlation Between the Expression of p27kip1 and Degree of Malignancy in Human Breast and Colorectal Cancers," *PNAS*, 1997, 94, 6380–6385.

(List continued on next page.)

Primary Examiner—Fiona T. Powers
(74) Attorney, Agent, or Firm—Woodcock Washburn Kurtz Mackiewicz & Norris LLP

(57) ABSTRACT

This invention relates to α-ketoamide inhibitors of multicatalytic protease (MCP), to compositions including such inhibitors, and to methods for the use of MCP inhibitors. The MCP inhibitors of the present invention are useful, for example, to retard loss of muscle mass incident to various physiological states.

32 Claims, 1 Drawing Sheet

OTHER PUBLICATIONS

Furono, K. et al., "Role of Different Proteolytic Systems in the Degradation of Muscle Proteins During Denervation Atrophy," *J. Biochem.*, 1990, 265(15), 8550–8557.

Glotzer, M. et al., "Cyclin is Degraded by the Ubiquitin Pathway," *Nature*, 1991, 349, 132–138.

Goldberg et al., "Proteolysis, Proteasomes and Antigen Presentation," *Nature*, 1992, 357, 375–379.

Goldberg et al., "Intracellular Protein Degradation in Mammalian and Bacterial Cells: Part 2," *Annu. Rev. Biochem.*, 1976, 45, 747–803.

Gonzalez et al., "Proteasome Activity is Required for the Stage–specific Transformation of a Protozoan Parasite," *J. Exp. Med.*, 1996, 184, 1909–1918.

Greenwald, "Superoxide Dismutase and Catalase as Therapeutic Agents for Human Diseases," *Free Rad. Biol. Med.*, 1990, 8, 201–209.

Halliwell et al., "Role of Free Radicals and Catalytic Metal Ions in Human Disease: An Overview," *Methods Enzymol.*, 1990, 186, 1–75.

Harbeson, S.L. et al., "Stereospecific Synthesis of Peptidyl α–Keto Amides as Inhibitors of Calpain", *J. Med. Chem.*, 1994, 37, 2918–2929.

Harding, C. et al., "Novel Dipeptide Aldehydes Are Proteasome Inhibitors and Block the MHC–I Antigen–Processing Pathway," *J. Immunol.*, 1995, 155, 1767–1775.

Harrison, D.J., "Molecular Mechanisms of Drug Resistance in Tumors," *J. Pathol.*, 1995, 175, 7–12.

Hershko, A. et al., "Mechanisms of Intracellular Protein Breakdown," *Annu. Rev. Biochem.*, 1982, 51, 335–364.

Hua et al., "Purification and Characterization of Proteasomes from Trypanosoma Brucei," *Mol. Biochem. Parasitol.*, 1996, 78, 33–46.

Hubbert, N. et al., "Human Papillomavirus Type 16 E6 Increases the Degradation Rate of p53 in Human Keratinocytes," *J. Virol.*, 1992, 66(10), 6237–6241.

Kumatori, A. et al., "Abnormally High Expression of Proteasomes in Human Leukemic Cells," *PNAS*, 1990, 87(18), 7071–7075.

Loda, M. et al., "Increased Proteasome–dependent Degradations of the Cyclin–Dependant Kinase Inhibitor p27 in Aggressive Colorectal Carcinomas," *Nature Med.*, 1997, 3(2), 231–234.

Lomo et al., "Characterization of A Multicatalytic Proteinase Complex (20S Proteasome) from Trypanosoma Brucei Brucei," *Immunopharmacology*, 1997, 36, 285–293.

Lopes, U. et al., "p53–dependent Induction of Apoptosis by Proteasome Inhibitors," *J. Biol. Chem.*, 1997, 272(20), 12893–12896.

Mori, M. et al., "p27 Expression and Gastric Carcinoma," *Nature Med.*, 1997, 3(6), 593.

Nabel, G. et al., "An Inducible Transcription Factor Activates Expression of Human Immunodeficiency Virus in T–Cells," *Nature*, 1987, 326, 711–713.

Orlowski, M., "The Multicatalytic Proteinase Complex, a Major Extralysosomal Proteolytic System," *Biochem.*, 1990, 29(45), 10289–10297.

Pagano, M. et al., "Role of the Ubiquitin–Proteasome Pathway in Regulating Abundance of the Cyclin–Dependent Kinase Inhibitor p27," *Science*, 1995, 269, 682–685.

Palombella, V. et al., The Ubiquitin–Proteasome Pathway Is Required for Processing the NF–kB1 Precursor Protein and the Activation of NF–kB *Cell*, 1994, 78, 773–785.

Porter P. et al., "Expression of Cell–Cycle Regulators p27kip1 and Cyclin E, Alone and in Combination, Correlate with Survival in Young Breast Cancer Patients," *Nature Med.*, 1997, 3(2), 222–225.

Rivett, A.J., "The Multicatalytic Proteinase," *J. Biol. Chem.*, 1989, 264(21), 12215–12219.

Rock, K. et al., "Inhibitors of the Proteasome Block the Degradation of Most Cell Proteins and the Generation of Peptides Presented on MHC Class I Molecules," *Cell*, 1994, 78, 761–771.

Rosen, D.R. et al., "Mutations in Cu/Zn Superoxide Dismutase Gene are Associated with Familial Amyotrophic Lateral Sclerosis," *Nature*, 1993, 362(6415), 59–62.

Schneffer, M. et al., "The HPV–16 E6 and E6–AP Complex Functions as a Ubiquitin–Protein Ligase in the Ubiquitination of p53," *Cell*, 1993, 75, 495–505.

Scheffner, M. et al., "The State of the p53 and Retinoblastoma Genes in Human Cervical Carcinoma Cell Lines," *PNAS*, 1991, 88, 5523–5527.

Shinorhara, K. et al., "Apoptosis Induction Resulting from Proteasome Inhibition," *Biochem. J.*, 1996, 317, 385–388.

To et al., "Identification and Characterization of an Activated 20S Proteasome in *Trypanosoma Brucei*," *FEBS Lett.*, 1997, 404, 253–262.

Van Antwerp, D. et al., "Suppression of TNF–a–Induced Apoptosis by NF–kB," *Science*, 1996, 274, 787–789.

Wang, C.Y. et al., "TNF– and Cancer Therapy–Induced Apoptosis: Potentiation by Inhibition of NF–kB," *Science*, 1996, 274, 784–787.

Green, T.W. et al., *Protective Groups in Organic Synthesis*, 2d. Ed., Wiley & Sons, 1991.

*Remington's Pharmaceutical Sciences*, Mack Publishing Company, Easton, PA, 1980.

Amparo, E. C. et al., "Preparation of .alpha.–aminoboronic acid and ester as inhibitors of thrombin", Chemical Abstract, 1996, vol. 125(17), p. 1172, Abstract No. 222432.

Amparo, E.C. et al., "Boronic acid and ester inhibitors of thrombin", Chemical Abstract, 1997, vol. 126(3), p. 594, Abstract No. 31466.

Nagase, H. et al., "Preparation of morphinan derivatives as analgesics and diuretics", Chemical Abstract, 1994, vol. 120(13), p. 1236, Abstract No. 164625.

Tsushima, T. et al., "Preparation of amino acid derivatives as digestive tract hormone antagonists", Chemical Abstract, 1992, vol. 116(25), p. 838, Abstract No. 256040.

Bihovsky et al., "Preparation of benzothiazine– and related heterocyclic group–containing amino acids as cysteine and serine protease inhibitors", Chemical Abstract, 1998, vol. 129, WO 98/21186, Abstract No. 28214.

\* cited by examiner

Anti-Tumor Growth Activity of Proteasome Inhibitors

Female C57BL mice bearing B16-F0 murine melanoma tumors were treated with either vehicle alone or Compound 1 at 10 mg/kg/day, ip, for 9 days. Tumor measurements were obtained at regular intervals as indicated.

Values are Mean ± SE of tumor volume.

*=p<0.05; **=p<0.01;, by Newman-Keuls test.

α-KETOAMIDE MULTICATALYTIC PROTEASE INHIBITORS

CROSS REFERENCE TO RELATED APPLICATIONS

This Application: is a divisional of U.S. provisional Application Ser. No. 09/167,163 filed Oct. 6, 1998, now U.S. Pat. No. 6,096,778, which claims benefit of U.S. Provisional Application Ser. No. 60/061,382 filed on Oct. 7, 1997, both of which are incorporated herein in their entirety.

FIELD OF THE INVENTION

This invention relates to α-ketoamide inhibitors of multicatalytic protease (MCP), to compositions including such inhibitors, and to methods for the use of MCP inhibitors. The MCP inhibitors of the present invention are useful, for example, to retard loss of muscle mass incident to various physiological states.

BACKGROUND OF THE INVENTION

Eukaryotic cells constantly degrade and replace cellular protein. This permits the cell to selectively and rapidly remove proteins and peptides having abnormal conformations, to exert control over metabolic pathways by adjusting levels of regulatory peptides, and to provide amino acids for energy when necessary, as in starvation. See Goldberg, A. L. & St. John, A. C. *Annu. Rev. Biochem.* 45:747–803 (1976). The cellular mechanisms of mammals allow for multiple pathways for protein breakdown. Some of these pathways appear to require energy input in the form of adenosine triphosphate ("ATP"). See Goldberg, A. L. & St. John, supra.

Multicatalytic protease (MCP, also referred to as "multicatalytic proteinase," "proteasome," "multicatalytic proteinase complex," "multicatalytic endopeptidase complex," "20S proteasome" and "ingensin") is a large molecular weight (700 kD) eukaryotic cytoplasmic proteinase complex which plays a role in at least two cellular pathways for the breakdown of protein to peptides and amino acids. See Orlowski, M. *Biochemistry* 29(45) 10289–10297 (1990). The complex has at least three different types of hydrolytic activities: (1) a trypsin-like activity wherein peptide bonds are cleaved at the carboxyl side of basic amino acids; (2) a chymotrypsin-like activity wherein peptide bonds are cleaved at the carboxyl side of hydrophobic amino acids; and (3) an activity wherein peptide bonds are cleaved at the carboxyl side of glutamic acid. See Rivett, A. J. *J. Biol. Chem.* 264:21 12215–12219 (1989) and Orlowski, supra.

One route of protein hydrolysis which involves MCP also involves the polypeptide "ubiquitin." Hershko, A. & Ciechanover A. *Annu. Rev. Biochem.* 51:335–364 (1982). This route, which requires MCP, ATP and ubiquitin, appears responsible for the degradation of highly abnormal proteins, certain short-lived normal proteins and the bulk of proteins in growing fibroblasts and maturing reticuloytes. See Driscoll, J. and Goldberg, A. L. *PNAS* 86:787–791 (1989). Proteins to be degraded by this pathway are covalently bound to ubiquitin via their lysine amino groups in an ATP-dependent manner. The ubiquitin-conjugated proteins are then degraded to small peptides by an ATP-dependent protease complex by the 26S proteasome, which contains MCP as its proteolytic core. Goldberg, A. L. & Rock, K. L. *Nature* 357:375–379 (1992).

A second route of protein degradation which requires MCP and ATP, but which does not require ubiquitin, has also been described. See Driscoll, J. & Goldberg, A. L., supra. In this process, MCP hydrolyzes proteins in an ATP-dependent manner. See Goldberg, A. L. & Rock, K. L., supra. This process has been observed in skeletal muscle. See Driscoll & Goldberg, supra. However, it has been suggested that in muscle, MCP functions synergistically with another protease, multipain, thus resulting in an accelerated breakdown of muscle protein. See Goldberg & Rock, supra.

The relative activities of cellular protein synthetic and degradative pathways determine whether protein is accumulated or lost. The abnormal loss of protein mass is associated with several disease states such as muscular dystrophy, cardiac cachexia, emphysema, leprosy, malnutrition, osteomalacia, child acute leukemia, and cancer cachexia. Loss of muscle mass is also observed in aging, long term hospitalization or long term confinement to bed, and in chronic lower back pain.

With denervation or disuse, skeletal muscles undergo rapid atrophy which leads to a profound decrease in size, protein content and contractile strength. This atrophy is an important component of many neuromuscular diseases in humans. Enhancement of protein breakdown has been implicated as the primary cause of muscle wasting in denervation atrophy, See Furono, K. et al. *J. Biochem.* 265/15:8550–8557 (1990). While the specific process or processes involved in protein hydrolysis in muscle has not been identified, evidence is available linking the involvement of MCP in the accelerated breakdown of muscle proteins. See, for example, Furono, supra, and PCT Published Application WO 92/20804 (publication date: Nov. 26, 1992).

The levels of several proteins responsible for cell cycle regulation are controlled through ubiquitin-dependent degradation by the proteasome. Among these proteasome substrates are the tumor supressor protein p53 (Schneffer, M. et al. *Cell* 75:495–505 (1993)), the cyclin-dependent kinase inhibitor p27 (Pagano, M. et al., *Science* 269:682–685 (1995), and cyclin B (Glotzer, M. et al., *Nature* 349:132–138 (1991). Inappropriate degradation of these key regulatory proteins by ubiquitin-dependent proteolysis has been correlated with the development of tumors in the case of p53 and human papillomavirus-containing cervical carcinomas (Schneffer, M. et al., *PNAS* 88: 5523–5527 (1991); Hubbert, N. et al., *J. Virol.* 66:6237–6241 (1992)) and in the example of p27 in colorectal carcinomas (Loda, M. et al., *Nature Med.* 3:231–234 (1997)). Additionally, high levels of p27 are associated with a positive clinical outcome in colon carcinoma (Loda, supra; Fredersdorf. S. et al., *PNAS* 94:6380–6385)), breast carcinomas (Catzavalos, C. et al. *Nature Med.* 3:227–230 (1997); Porter, P. et al., *Nature Med.* 3:222–225 (1997); Fredersdorf, supra) and gastric carcinoma (Mori, M. et al. *Nature Med.* 3:593 (1997)). Treatment of transformed cells with proteasome inhibitors has been reported to result in accumulation of p27 (Drexler, H. C. A. *PNAS* 94:855–860 (1997)) and p53 (Shinohara, K. et al. *Biochem J.* 317:385–388 (1996); Lopes, U. et al. *J. Biol. Chem.* 272:12893–12896 (1997)) and to trigger apoptotic death of the cells. Therefore, compounds which inhibit the degradation of these growth inhibitory factors would be expected to cause cell cycle arrest and would be useful in the treatment of cancer and other proliferative diseases, including psoriasis and restenosis.

The transcription factor NF-κB stimulates expression of a wide variety of genes important in immune and inflammatory responses (Bauerle, P. and Henkel, T. *Annu. Rev. Immunol.* 12:141–179 (1994)). In unstimulated cells, NF-κB exists as an inactive cytoplasmic complex with an inhibitor protein, IκB. Upon stimulation of the cells, the IκB protein is ubiquitinated and degraded by the proteasome, activating NF-κB (Palombella, V. et al. *Cell* 78:773–785 (1994)). The resulting free NF-κB enters the cell nucleus where it initiates transcription.

Activation of NF-κB results in production of inflammatory cytokines such as tumor necrosis factor a, interleukin-2 and interleukin-6, and cell adhesion molecules including intracellular cell adhesion molecule 1 (ICAM-1), vascular cell adhesion molecule 1-(VCAM-2), and E-selectin (Baeuerle and Henkel, supra). Suppression of the activation of NF-κB through inhibition of the proteasome would therefore provide a method for treatment of inflammatory conditions including arthritis, sepsis, and inflammatory bowel disease.

Activation of the cellular apoptotic program is a current strategy for treatment of human cancers. It has been demonstrated that X-irradiation and standard chemotherapeutic drugs kill some tumor cells through induction of apoptosis (Fisher, D. E. *Cell* 78, 539–542 (1994)). Unfortunately, the majority of human cancers at present are resistant to these therapies (Harrison, D. J. J. *Patho.* 175, 7–12(1995)). Activation of NF-κB has been demonstrated to render some tumor cells resistant to the pro-apoptotic effects of TNF-α, cancer chemotherapeutic agents and radiation (Beg, A. And Baltimore, D. *Science* 274, 782–784(1996); Wang, C. Y. et al., *Science* 274, 784–787 (1996); Van Antwerp D., et al., *Science* 274, 787–789 (1996)). Administration of proteasome inhibitors to patients with cancer in combination with ionizing radiation or other chemotherapeutic drugs might enhance the efficacy of the pro-apoptotic agent.

Activated NF-κB is also required for replication of the human immunodeficiency virus (HIV) (Nabel, G. and Baltimore, D. *Nature* 326:711–713 (1987)). A process which inhibits activation of NF-κB could therefore be therapeutically beneficial to patients infected with HIV.

Cytosolic antigens are processed through ubiquitination and proteasome-catalyzed cleavage into peptides which are transported to the endoplasmic reticulum and bound to the MHC-1 complex. Proteasome inhibitors prevent MHC-1 antigen presentation without effect on MHC-II antigen processing (Rock, K. et al. *Cell* 78:761–771 (1994); Harding, C. et al. *J. Immunol.* 155:1767–1775 (1995)). Such inhibitors should therefore be useful in the treatment of diseases resulting from inappropriate antigen presentation, including autoimmune diseases and rejection of transplants.

Proteasome activity also is required in the life cycle of many parasitic organisms. For example, both the bloodstream and insect forms of the protozoan parasite Trypanasoma brucei encode a 20S proteasome which is believed to be required for the organism's survival (Hua et al. *Mol. Biochem. Parasitol.* 78, 33–46(1996); Lomo et al. *Immunopharmacology* 36, 285–293(1997); To and Wang *FEBS Lett.* 404, 253–262(1997)). Inhibitors of the proteasome have been demonstrated to prevent the transformation of Trypanosoma cruzi trypomastigotes into amastigotes, and the intracellular development of amastigotes into trypomastigotes (Gonzalez et al. *J. Exp. Med.* 184, 1909–1918 (1996)). Proteasome inhibitors should therefore have utility in the treatment of diseases resulting from parasitic infections including, but not limited to, African sleeping sickness and malaria.

MCP activity has been implicated in several disease states. For example, abnormally high expression of MCP in human leukemic cell lines has been reported. Kumatori, A. et al. *PNAS* 87:7071–7075 (1990). Autoantibodies against MCP in patients with systemic-lupus erythematosus ("SLE") have also been reported. Arribas, J. et al. *J. Exp. Med.* 173:423–427 (1990).

Agents which are capable of inhibiting the MCP complex are needed; such agents would provide a valuable tool for both those conducting research in the area of, for example, MCP activity, as well as those in the medical fields in order to, for example, control the deleterious effects of abnormal or aberrant MCP activity. The present invention is directed to these important ends.

SUMMARY OF THE INVENTION

The present invention is directed to novel α-ketoamide multicatalytic protease ("MCP") inhibitors. The subject invention also comprises methods for inhibition of MCP associated with certain disorders, including the treatment of muscle wasting disorders.

In one aspect are provided compounds having the Formula I:

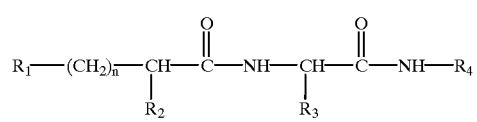

wherein:

$R_1$ is selected from the group consisting of —C≡N, —C(=O)OR$_8$, phthalimido, —NHSO$_2$R$_8$, and —NH—J;

$R_2$ is selected from the group consisting of H, hydroxyl, alkyl having from one to ten carbons and cycloalkyl having from three to seven carbons;

$R_3$ is selected from the group consisting of —(CH$_2$)$_m$—NHC(=N—R$_5$)—NH$_2$, —R$_6$—H, —R$_6$—J, —R$_{12}$—(J)$_2$, —R$_6$—NO$_2$, —R$_6$—CN, —(CH$_2$)$_m$—NH$_2$, and —(CH$_2$)$_m$—NH—J;

$R_4$ is —CH(CH$_2$R$_7$)—Q;

$R_5$ is selected from the group consisting of —NO$_2$, —CN, and —J;

R, is —(CH$_2$)$_m$—NH—C(=NH)—NH—;

$R_{12}$ is —(CH$_2$)$_m$—NH—C(=NH)—N—;

Q is —C(=O)C(=O)NH—X—A—Y;

$R_7$ is selected from the group consisting of phenyl, and alkyl having from one to eight carbons, said alkyl group being optionally substituted with one or more halogen atoms, aryl, or heteroaryl groups;

$R_8$ is selected from the group consisting of hydrogen and alkyl having from one to six carbons, said alkyl group being optionally substituted with one or more halogen atoms, aryl or heteroaryl groups;

X is a bond or —O—;

A is an alkylene group of 1 to 8 carbons, said alkylene group being optionally substituted with one or more halogen atoms, aryl, or heteroaryl groups;

Y is N ($R_{13}$)—G;

G is selected from the group consisting of H, a blocking group, $SO_2R_9$, —C(=O)$NHR_{10}$, —C(=S)$NHR_{10}$, and —COORS;

or the moiety —A—Y forms a 5-, 6-, or 7-membered lactam ring;

$R_9$ is selected from the group consisting of alkyl, aryl, and heteroaryl, said alkyl, aryl, or heteroaryl groups being optionally substituted with K;

$R_{10}$ is selected from the group consisting of H, alkyl, aryl, and heteroaryl, said alkyl, aryl, or heteroaryl groups being optionally substituted with K;

$R_{13}$ is selected from the group consisting of H and lower alkyl;

J is a blocking group;

K is selected from the group consisting of halogen, $CO_2R_{10}$, $R_{10}OC(=O)$, $R_{10}OC(=O)$ NH, OH, CN, $NO_2$, $NR_{10}R_{11}$, N=C($NR_{10}R_{11})_2$, $SR_{10}$, $OR_{10}$, phenyl, naphthyl, heteroaryl, and a cycloalkyl group having from 3 to 8 carbon atoms;

$R_{11}$ is the same as $R_{10}$;

n is an integer from 5 to 10;

m is an integer from 2 to 5; or a pharmaceutically acceptable salt thereof; with the proviso that when X is a bond and $R_3$ is —$R_6$—H or —$(CH_2)_m$—$NH_2$, then G is $SO_2R_9$.

In some preferred embodiments of the compounds of Formula I, $R_1$ is phthalimido, —C≡N, —C(=O)$OCH_3$, or —$NHSO_2CF_3$. In further preferred embodiments of the compounds of Formula I, $R_2$ is H or cyclopentyl.

In some preferred embodiments of the compounds of Formula I, $R_3$ is —$R_6$—J, —$R_6$—$NO_2$, —$R_6$—H, —$R_{12}$—$(J)_2$, —$(CH_2)_m$—NH—J, or —$(CH)_m$—$NH_2$, wherein J is preferably Boc, methylsulfonyl or pyrazinoyl.

In some preferred embodiments of the compounds of Formula I, $R_7$ is phenyl or lower alkyl, with isopropyl being preferred.

In some preferred embodiments of the compounds of Formula I, X is a bond. In further preferred embodiments of the compounds of Formula I, A is —$CH_2CH_2$—.

G is preferably $SO_2$-aryl, with $SO_2$-phenyl being preferred. In more preferred embodiments, the aryl or phenyl groups are optionally substituted, preferably by one or more halogen atoms.

In further preferred embodiments of the compounds of Formula I, G is H or a blocking group, with t-Boc being preferred.

In some preferred embodiments, the moiety —A—Y forms a 5-, 6-, or 7-membered lactam ring, which preferably has the structure:

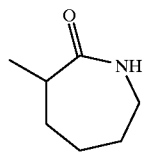

More preferred are the substituents shown for the compounds described in the Examples, infra, with the substituents shown in Examples 1–8 being particularly preferred.

In particularly preferred embodiments of the compounds of Formula I, X is a bond; A is —$CH_2CH_2$—; n is 8; $R_1$ is phthalimido; $R_2$ is cycloalkyl with cyclopentyl being especially preferred; G is H, t-Boc or $SO_2R_9$ where $R_9$ is phenyl optionally subsituted with halogen; $R_7$ is phenyl or alkyl with isopropyl being preferred; and $R_3$ is —(CH-)$_m$—NHC(=NH)—$NO_2$, —$(CH_2)_m$—NHC(=NH)—N(Boc)$_2$, —$(CH_2)_m$—NHC(=NH)—$NH_3Cl$, —$(CH_2)_m$—$NH_3Cl$, or —$(CH_2)_m$—NH—J where J is Boc, methylsulfonyl or pyrazinoyl.

Some especially preferred substituents for $R_1$–$R_4$ in the compounds of Formula I are those shown for compounds 1, 14, 17, 19, 20, 28, 34, 35, 36, and 37–9, infra.

The compounds of the invention are useful in a variety of applications. For example, the compounds may be employed in research applications to further refine and develop in vitro and in vivo models for mechanistic understanding of the MCP pathway and for presentation of peptide antigens via the major histocompatibility complex class I (MHC I) pathway.

In a therapeutic setting, compounds of the invention can be utilized to alleviate, mediate, reduce and/or prevent disorders which are associated with normal, abnormal and/or aberrant activity of MCP. For example, compositions comprising the claimed compounds can be used for inhibiting MCP activity, for treatment of inflammatory conditions including arthritis, sepsis, and inflammatory bowel disease, as potent inducers of apoptosis in a variety of tumor cells, thus providing utility as anti-tumor agents, for decreasing the loss of muscle mass, treating muscle wasting disorders, reducing superoxide dismutase degradation and treating disorders characterized by a reduction of superoxide dismutase activity. In preferred embodiments, compositions are provided for inhibiting MCP comprising a compound of the invention. In other preferred embodiments, methods are provided for inhibiting MCP comprising contacting MCP with an inhibitory amount of a compound of the invention.

Methodologies for making the present α-ketoamide inhibitors are also disclosed. Other useful methodologies will be apparent to those skilled in the art, once armed with the present disclosure. These and other features of the compounds of the subject invention are set forth in more detail below.

DETAILED DESCRIPTION

Figure 1:
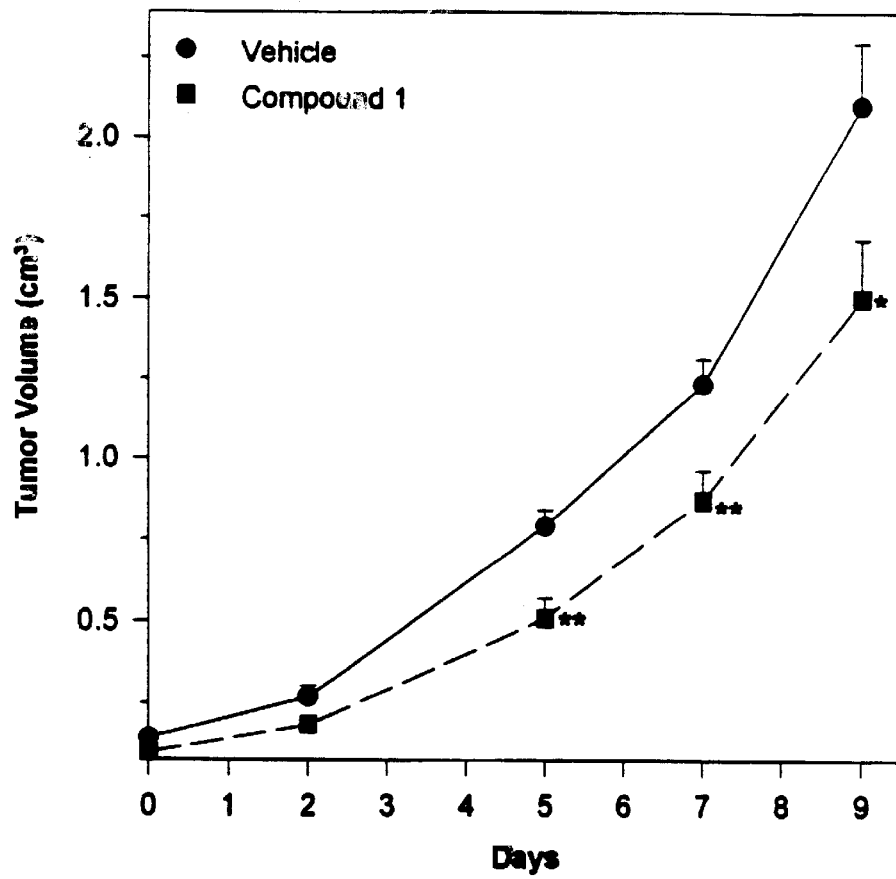
FIG. 1 is shows the results from the in vivo study wherein Female C57BL mice bearing B16-F0 murine melanoma tumors were treated with either vehicle alone or Compound 1 at 10 mg/kg/day, ip, for 9 days.

This invention provides MCP inhibitors, compositions including these inhibitors and methods of using these inhibitors. In one aspect of the present invention, MCP inhibitors are provided having the Formula I:

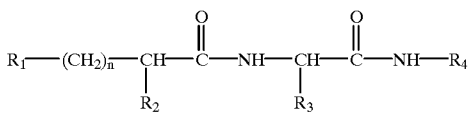

wherein:
- $R_1$ is selected from the group consisting of —C≡N, —C(=O)OR$_8$, phthalimido, —NHSO$_2$R$_8$, and —NH—J;
- $R_2$ is selected from the group consisting of H, hydroxyl, alkyl having from one to ten carbons and cycloalkyl having from three to seven carbons;
- $R_3$ is selected from the group consisting of —(CH$_2$)$_m$—NHC(=N—R$_5$)—NH$_2$, —R$_6$—H, —R$_6$—J, —R$_{12}$—(J)$_2$, —R$_6$—NO$_2$, —R$_6$—CN, —(CH$_2$)$_m$—NH$_7$, and —(CH$_2$)$_m$—NH—J;
- $R_4$ is —CH(CH$_2$R$_7$)—Q;
  - $R_5$ is selected from the group consisting of —NO$_2$—, —CN, and —J;
  - $R_6$ is —(CH$_2$)$_m$—NH—C(=NH)—NH—;
  - $R_{12}$ is —(CH$_2$)$_m$—NH—C(=NH)—N—;
- Q is —C(=O)C(=O)NH—X—A—Y;
- $R_7$ is selected from the group consisting of phenyl, and alkyl having from one to eight carbons, said alkyl group being optionally substituted with one or more halogen atoms, aryl, or heteroaryl groups;
- $R_8$ is selected from the group consisting of hydrogen and alkyl having from one to six carbons, said alkyl group being optionally substiuted with one or more halogen atoms, aryl or heteroaryl groups;
- X is a bond or —O—;
- A is an alkylene group of 1 to 8 carbons, said alkylene group being optionally substituted with one or more halogen atoms, aryl, or heteroaryl groups;
- Y is N(R$_{13}$)—G;
- G is selected from the group consisting of H, a blocking group., SO$_2$R$_9$, —C(=O)NHR$_{10}$, —C(=S)NHR$_{10}$, and —CO$_2$R$_9$;
- or the moiety —A—Y forms a 5-, 6-, or 7-membered lactam ring;
- $R_9$ is selected from the group consisting of alkyl, aryl, and heteroaryl, said alkyl, aryl, or heteroaryl groups being optionally substituted with K;
- $R_{10}$ is selected from the group consisting of H, alkyl, aryl, and heteroaryl, said alkyl, aryl, or heteroaryl groups being optionally substituted with K;
- $R_{13}$ is selected from the group consisting of H and lower alkyl;
- J is a blocking group;
- K is selected from the group consisting of halogen, CO$_2$R$_{10}$, R$_{10}$C(=O), R$_{10}$C(=O)NH, OH, CN, NO$_2$, NR$_{10}$R$_{11}$, N=C(NR$_{10}$R$_{11}$)$_2$, SR$_{10}$, OR$_{10}$, phenyl, naphthyl, heteroaryl, and a cycloalkyl group having from 3 to 8 carbon atoms;
- $R_{11}$ is the same as $R_{10}$;
- n is an integer from 5 to 10;
- m is an integer from 2 to 5;

or a pharmaceutically acceptable salt thereof; with the proviso that when X is a bond and $R_3$ is —R$_6$—H or —(CH$_2$)$_m$—NH$_2$, then G is SO$_2$R$_9$.

It is recognized that various steroisomeric forms of the compounds of Formula I may exist. Preferred compounds of the invention have the L-configuration at the carbon to which the substituent $R_3$ is attached. However, reacemates and individual enantiomers and mixtures thereof form part of the present invention.

As used herein, the term "alkyl" includes straight-chain, branched and cyclic hydrocarbon groups such as, for example, methyl, ethyl, propyl, isopropyl, butyl, isobutyl, sec-butyl, tert-butyl, pentyl, 1-ethylpentyl, hexyl, octyl, cyclopropyl, methylcyclopentyl, and cyclohexyl groups. Preferred alkyl groups have 1 to about 10 carbon atoms. More preferred are "lower alkyl" groups which preferably have from 1 to about 6 carbon atoms. As used herein, the term "akylene" denotes branched or unbranched hydrocarbon groups having 1 to about 8 carbon atoms such as, for example, ethylene (—CH$_2$CH$_2$—), propylene, butylene, hexylene, 1-methylethylene, 2-methylethylene, and 2-methylpropylene. "Acyl" groups are alkylcarbonyl groups. "Aryl" groups are aromatic cyclic compounds including but not limited to phenyl, tolyl, naphthyl, anthracyl, phenanthryl, and pyrenyl. Also included within the definition of "aryl" are ring systems havoing two aromatic rings connected by a bond, such as biphenyl. Preferred aryl groups include phenyl and naphthyl.

The term "carbocyclic", as used herein, refers to cyclic groups in which the ring portion is composed solely of carbon atoms. The term "halogen" refers to F, Cl, Br, and I atoms. The term "arylalkyl" denotes alkyl groups which bear aryl groups, for example, benzyl groups. As used herein, "alkoxy" groups are alkyl groups linked through an oxygen atom. Examples of alkoxy groups include methoxy (—OCH$_3$) and ethoxy (—OCH$_2$CH$_3$) groups. In general, the term "oxy" when used as a suffix denotes attachment through an oxygen atom. Thus, alkoxycarbonyl groups are carbonyl groups which contain an alkoxy substituent, i.e., groups of general formula —C(=O)—O—R, where R is alkyl. The term "alkoxyalkyl" as used herein denotes an alkoxy group attached to an alkyl group. The term "aryloxy" denotes an aryl group linked through an oxygen atom, and the term "arylalkyloxy" denotes an arylalkyl group linked through an oxygen atom.

The terms "heterocycle", "heterocyclyl", and "heterocyclic" refer to cyclic groups in which a ring portion includes at least one heteroatom such as 0, N or S. Heterocyclic groups include "heteroaryl" as well as "heteroalkyl" groups. The term "heteroaryl" denotes aryl groups having one or more hetero atoms (e.g., O, N, or S) contained within an aromatic ring. Also included within the definition of "heteroaryl" are ring systems having two aromatic rings connected by a bond, where at least one of the rings contains a hetero atom. Preferred "heteroaryl" groups include pyridyl, pyrimidyl, pyrrolyl, furyl, thienyl, imidazolyl, triazolyl, tetrazolyl, quinolyl, isoquinolyl, benzoimidazolyl, thiazolyl, bipyridyl, pyridylthiophenyl, pyrimidylthiophenyl, isoxazolylthiophenyl, pyrazolylthiophenyl, phthalimido, and benzothiazolyl. The term "heterocycloalkyl" denotes a heterocycle attached through a lower alkyl group. The term "heteroarylalkyl" denotes a heteroaryl group attached through an alkyl group. As used herein, the term "heteroalkyl" denotes a heterocyclic group which contains at least one saturated carbon atom in a heterocyclic ring. Examples of heteroalkyl groups include piperidine, dihydropyridine, and tetrahydroisoquinyl groups.

Functional groups present in the compounds of Formula I may contain blocking groups. Blocking groups are known per se as chemical functional groups that can be selectively appended to functionalities, such as hydroxyl groups, amino groups, thio groups, and carboxyl groups. Protecting groups are blocking groups which can be readily removed from functionalities. These groups are present in a chemical compound to render such functionality inert to chemical reaction conditions to which the compound is exposed. Any of a variety of protecting groups may be employed with the present invention. Examples of such protecting groups are the benzyloxycarbonyl (Cbz; Z), toluenesulfonyl, t-butoxycarbonyl, methyl ester, and benzyl ether groups. Other preferred protecting groups according to the invention may be found in Greene, T. W. and Wuts, P. G. M., "*Protective Groups in Organic Synthesis*" 2d. Ed., Wiley & Sons, 1991.

Further blocking groups useful in the compounds of the present invention include those that bear acyl, aroyl, heteroaroyl, alkyl, alkanesulfonyl, arylalkanesulfonyl, or arylsulfonyl substituents on their amino groups. Other useful blocking groups include alkyl ethers, e.g., the methyl ether of serine.

As previously indicated, MCP activity has been linked with a variety of disorders and diseases. Because compounds as disclosed herein are useful in inhibiting the activity of MCP, and because the usefulness of such compounds can be applied to both research and therapeutic settings, methodologies for inhibiting the activity of MCP by contacting the MCP with a compound of the invention include providing the compound to a mammal, including a human, as a medicament or pharmaceutical agent.

As used herein, the term "contacting" means directly or indirectly causing placement together of moieties to be contacted, such that the moieties come into physical contact with each other. Contacting thus includes physical acts such as placing the moieties together in a container, or administering moieties to a patient. Thus, for example, administering a compound of the invention to a human patient evidencing a disease or disorder associated with abnormal and/or aberrant activities of MCP which are associated with such disease or disorder, falls within the scope of the definition of term "contacting."

In preferred embodiments, pharmaceutical compositions according to the invention are administered to patients suffering from a disorder, i.e., an abnormal physical condition, a disease or pathophysiological condition associated with abnormal and/or aberrant activities of MCP. The disorders for which the compositions of the invention are administered are preferably those which directly or indirectly produce a wasting (i.e., loss) of muscle mass, that is, a muscle wasting disorder. These include muscular dystrophies, cardiac cachexia, emphysema, leprosy, malnutrition, osteomalacia, child acute leukemia, AIDS cachexia and cancer cachexia.

In the context of the invention, "administering" means introduction of the pharmaceutical composition into a patient. Preferred methods of administration include intravenous, subcutaneous and intramuscular administration. Preferably the compound will be administered as a pharmaceutical composition comprising the compound in combination with a pharmaceutically acceptable carrier, such as physiological saline. Other suitable carriers can be found in *Remington's Pharmaceutical Sciences* (Mack Pub. Co., Easton, Pa., 1980).

The concentrations of the compounds described herein in a pharmaceutical composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 $\mu$g/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration. As used herein the term "patient" denotes any type of vertabrate. Preferably, the patient is a human. The muscular dystrophies are genetic diseases which are characterized by progressive weakness and degeneration of muscle fibers without evidence of neural degeneration. In Duchenne muscular dystrophy (DMD) patients display an average of a 67% reduction in muscle mass, and in myotonic dystrophy, fractional muscle protein synthesis has been shown to be decreased by an average of 28%, without any corresponding decrease in non-muscle protein synthesis (possibly due to impaired end-organ response to anabolic hormones or substrates). Accelerated protein degradation has been demonstrated in the muscles of DMD patients.

Severe congestive heart failure (CHF) is characterized by a "cardiac cachexia," i.e., a muscle protein wasting of both the cardiac and skeletal muscles, with an average 19% body weight decrease. The cardiac cachexia is caused by an increased rate of myofibrillar protein breakdown.

Emphysema is a chronic obstructive pulmonary disease, defined by an enlargement of the air spaces distal to the terminal non-respiratory bronchioles, accompanied by destructive changes of the alveolar walls. Clinical manifestations of reduced pulmonary functioning include coughing, wheezing, recurrent respiratory infections, edema, and functional impairment and shortened life-span. The efflux of tyrosine is increased by 47% in emphysematous patients. Also, whole body leucine flux remains normal, whole-body leucine oxidation is increased, and whole-body protein synthesis is decreased. The result is a decrease in muscle protein synthesis, accompanied by a decrease in whole body protein turnover and skeletal muscle mass. This decrease becomes increasingly evident with disease progression and long term deterioration.

In diabetes mellitus, there is a generalized wasting of small muscle of the hands, which is due to chronic partial denervation (neuropathy). This is most evident and worsens with long term disease progression and severity. Leprosy is associated with a muscular wasting which occurs between the metacarpals of the thumb and index finger. Severe malnutrition is characterized by, inter alia, severe muscle wasting.

Osteomalacia is a nutritional disorder caused by a deficiency of vitamin D and calcium. It is referred to as "rickets" in children and "osteomalacia" in adults. It is marked by a softening of the bones (due to impaired mineralization, with excess accumulation of osteoid), pain, tenderness, muscle wasting and weakness, anorexia, and overall weight loss. It can result from malnutrition, repeated pregnancies and lactation (exhausting or depleting vitamin D and calcium stores), and vitamin D resistance.

In childhood acute leukemia there is protein energy malnutrition which results in skeletal muscle wasting. Studies have shown that some children exhibit the muscle wasting even before diagnosis of the leukemia, with an average 27% decrease in muscle mass. There is also a simultaneous 33%–37% increase in adipose tissue, resulting in no net change in relative body weight and limb circumference.

Cancer cachexia is a complex syndrome which occurs with variable incidence in patients with solid tumors and hematological malignancies. Clinically, cancer cachexia is manifested as weight loss with massive depletion of both adipose tissue and lean muscle mass, and is one cause of death which results from cancer. Cancer cachexia patients have shorter survival times, and decreased response to chemotherapy. In addition to disorders which produce muscle wasting, other circumstances and conditions appear to be linked in some fashion with a decrease in muscle mass. Such afflictions include muscle wasting due to chronic back pain, advanced age, long term hospitalization due to illness or injury, alcoholism and corticosteroid therapy.

Studies have shown that in severe cases of chronic lower back pain, there is paraspinal muscle wasting. Decreasing paraspinal muscle wasting alleviates pain and improves function.

It is also believed that general weakness in old age is due to muscle wasting. As the body ages, an increasing proportion of skeletal muscle is replaced by fibrous tissue. The result is a significant reduction in muscle power, but only a marginal rejection in fat-free mass.

Studies have shown that in patients suffering injuries or chronic illnesses, and hospitalized for long periods of time, there is long-lasting unilateral muscle wasting, with an average 31% decrease in muscle mass. Studies have also shown that this can be corrected with intensive physiotherapy. However, it may be more effective for many patients to effect improvement with drug therapy.

In alcoholics there is wasting of the anterior tibial muscle. This proximal muscle damage is caused by neurogenic damage, namely, impaired glycolytic and phosphorylase enzyme activity. The damage becomes apparent and worsens the longer the duration of the alcohol abuse. Patients treated with corticosteroids experience loss of muscle mass.

MCP has been shown to activate the intracellular mediator of inflammation referred to as $NF_{kappa}B$. (See Baeuerle, P. A. and Henkel, T. (1994) *Annu. Rev. Immunol.* 12, 141–179.) Inhibitors of MCP therefore potentially have use in the treatment of autoimmune and inflammatory diseases.

The compounds of the invention can be used to alleviate the muscle mass loss resulting from the foregoing conditions, as well as others. Additionally, the MCP inhibitors of the invention are useful in veterinary and animal husbandry applications to, e.g., counter weight loss in animals, or to promote growth.

MCP has been implicated in the presentation of peptide antigens via the major histocompatibility complex class I (MHC I) pathway. See Goldberg and Rock, supra; see also Rock et al., *Cell,* 78: 761–771 (1994) hereinafter "Rock et al." Inhibitors of MCP therefore have utility as research reagents in studies where inhibition of the MHC I pathway is desired as well as in the alleviation of diseases and disorders which are associated with aberrant and/or abnormal MHC-I processing of antigens. Because the precise origin of most of the peptides presented on MHC-I molecules is still not clear and because evidence has recently accumulated that MCP may play a role in MHC-I presentation (see Rock et al. supra), reagents such as the disclosed MCP inhibitors which block the proteolytic processing of antigens for MHC-I presentation would be useful in resolving the importance of this pathway.

MCP inhibitors of the invention are also useful in enhancing the activity of Cu/Zn superoxide dismutase-l ("SOD-1") enzyme. Accordingly, these compounds are useful in both research settings for the investigation of SOD-1 deficient systems and in the treatment of neurodegenerative or other disorders characterized by a reduction in SOD-1 enzyme activity (i.e., wherein such a reduction has been implicated in the pathogenesis of the disorder). Such conditions include diseases involving oxidative stress such as Parkinson's disease, Alzheimers's disease, Huntington's disease, stroke, trauma, amyotrophic lateral sclerosis and ischemia.

SOD-1 is a homodimeric metalloenzyme that catalyzes the dismutation of the toxic superoxide anion $O_2^-$ to $O_2$ and $H_2O_2$. SOD-1 is a scavenger of free radicals and therefore acts as a first line defense in the detoxification of superoxide radicals, which are normal by-products of aerobic metabolism. SOD-1 occurs primarily in eukaryotes and is found in the cytoplasm of virtually all cell types. SOD-1 is an essential enzyme in the physiological response to oxygen toxicity and has been actively investigated as a therapeutic agent in pathological conditions related to oxidative stress. See Bannister et al., *CRC Crit. Rev. Biochem.* 22:111–180 (1987); Halliwell et al., *Methods in Enzymol.,* 186:1–75 (1990); Greenwald, *Free Rad. Biol. Med.* 8:201–209 (1990).

Features that have prevented the use of SOD-1 as a therapeutic agent are its poor intracellular access when supplied exogenously, and its extremely short half-life in serum. Therefore, compounds that enhance the activity of intracellular SOD-1 would provide a significant advancement in SOD-1 therapy.

ALS is a progressive paralytic disorder caused by degeneration of large motor neurons of the spinal cord and brain. Approximately 5–10% of ALS cases are familial (FALS) and are inherited as an autosomal dominant trait. Recently, sixteen different missense mutations have been identified in a subset of families with FALS and occur within the gene encoding SOD-1. See Rosen, D. R., et al., *Science* 261:1047–1051 (1993); Deng, H. -X., et al., *Nature* 362:59–62 (1993). These mutations lead to a decrease in SOD-1 activity in red blood cells and brain tissue, and have been shown to destabilize the SOD-1 protein resulting in increased turnover of the enzyme. See Bowling, A. C., et al., *J. Neurochem.* 61:2322–2325 (1993); Borchelt, D. R., et al., *Proc. Natl. Acad. Sci.* 91:8292–8296 (1994). Additionally, a transgenic-mouse model of ALS, based upon the implication of the connection between SOD-1 and ALS, has been described. Brown, R. H. 331/16 *NEJM* 1091 (1994).

The invention is further illustrated by way of the following examples. These examples are intended to elucidate the invention. The examples are not intended to limit the scope of the claims.

EXAMPLES

General Methods.

Thin layer chromatography was performed on silica gel plates (MK6F 60A, size 1×3 in, layer thickness 250 μm, Whatman Inc.). Preparative thin layer chromatography was performed on silica gel plates (size 20×20 in, layer thickness 1000 micron, Analtech). Preparative column chromatography was carried out using Merck silica gel, 40–63 μm, 230–400 mesh. $^1$H NMR spectra were recorded on a GE QE Plus instrument (300 MHz) using tetramethylsilane as internal standard. Electrospray mass spectra were recorded on a VG platform II instrument (Fisons Instruments).

Example 1

Preparation of Compound 1

Compound 1 was assembled from building blocks 2, 3, 4 and 5, as shown in scheme 1, below:

Scheme 1

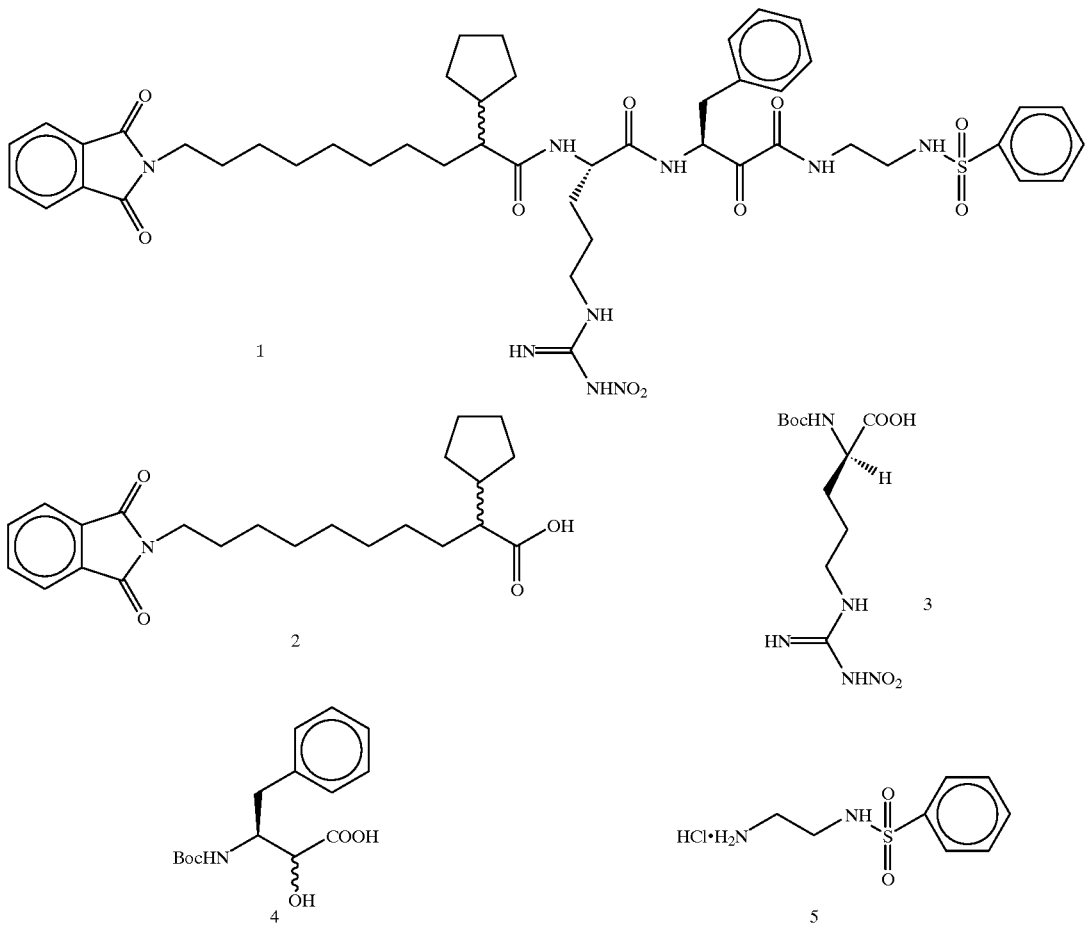

Preparation of Compound 2

The preparation of compound 2, as a racemate, is described in U.S. Pat. No. 5,550,262, which is incorporated by reference herein in its entirety.

Preparation of Compound 3

Compound 3 was purchased from NovaBiochem, San Diego, Calif.

Preparation of Compound 4

Compound 4 and related a-hydroxy acids were prepared following a general procedure of Harbeson et al, *J. Med. Chem.* 1994, 37, 2918–2929, which is incorporated herein by reference in its entirety.

Preparation of Compound 5

The preparation of compound 5 is depicted in scheme 2, below:

Scheme 2

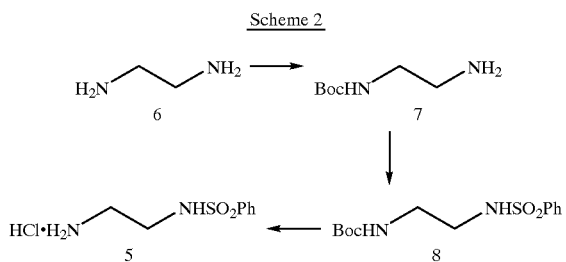

Preparation of Compound 7

To a solution of 1,2-ethylenediamine (6, 10.80 g, 12.00 mL, 0.18 mol) in THF (30 mL) was added slowly BOC-ON (22.10 g, 0.09 mol) in THF (70 mL) over a period of 4 hours. The reaction mixture was stirred overnight, concentrated on a rotavapor, and taken up into water (150 mL). The aqueous layer was acidified (pH~S-6) with solid citric acid monohydrate, washed with ether (3×50 mL), and then treated (at 0° C.) with 6 N NaOH solution to make it basic (pH~12–13). The basic solution was extracted into ethyl acetate (3×100 mL), and the combined ethyl acetate layer was dried (MgSO$_4$) and concentrated to generate 7.23 g of monoprotected diamine 7.

Compound 7: semisolid; $^1$H-NMR (CDDl$_3$) δ 5.00 (broad, 1H), 3.20 (broad q, 2H), 2.80 (t, 2H), 1.45 (s, 9H), 1.25 (broad, 2H).

Preparation of Compound 8

A cooled (0–5° C.) solution of the amine 7 (0.321 g, 0.002 mol) in methylene chloride (5 mL) was treated sequentially with triethylamine (0.243 g, 0.33 mL, 0.0024 mol) and benzenesulfonyl chloride (0.423 g, 0.30 mL, 0.0024 mol). The ice-bath was removed and the solution was stirred for an additional 0.5 hour and then washed successivly with water (2×5 mL), cold (0–5° C.) 0.5 N HCl (1×5 mL), 2% NaHCO$_3$ solution (1×5 mL), and brine (1×5 mL). The solution was dried over MgSO$_4$ and the solvent evaporated to give a residue which was washed several times with n-pentane to generate 0.60 g of the sulfonamide derivative 8.

Compound 8: white solid, mp 92–95° C.; R$_f$ (TLC, 5% methanol in methylene chloride) 0.55; $^1$H-NMR (CDCl$_3$) δ 7.85 (d, 2H), 7.55 (m, 3H), 5.30 (broad d, 1H), 4.85 (broad, 1H), 3.25 (broad q, 2H), 3.10 (broad q, 2H), 1.40 (s, 9H).

Preparation of Compound 5

A solution of compound 8 (0.560 g, 0.0019 mol) in 1,4-dioxane (4 mL) was treated with 4 N HCl in dioxane (4 mL). The mixture was stirred at room temperature for 1 hour and concentrated at the rotavapor. The residue was washed several times with ethyl acetate and dried under vacuum to generate 0.40 g of the amine salt 5.

Compound 5: white solid, mp 178–180° C.; $^1$H-NMR (DMSO-d$_6$) δ 8.20–8.00 (broad t, 4H), 7.80 (d, 2H), 7.60 (m, 3H), 2.95 (broad q, 2H), 2.80 (broad, 2H).

Coupling of the building blocks 4, 5, 3 and 2 is shown in Scheme 3, below:

Scheme 3

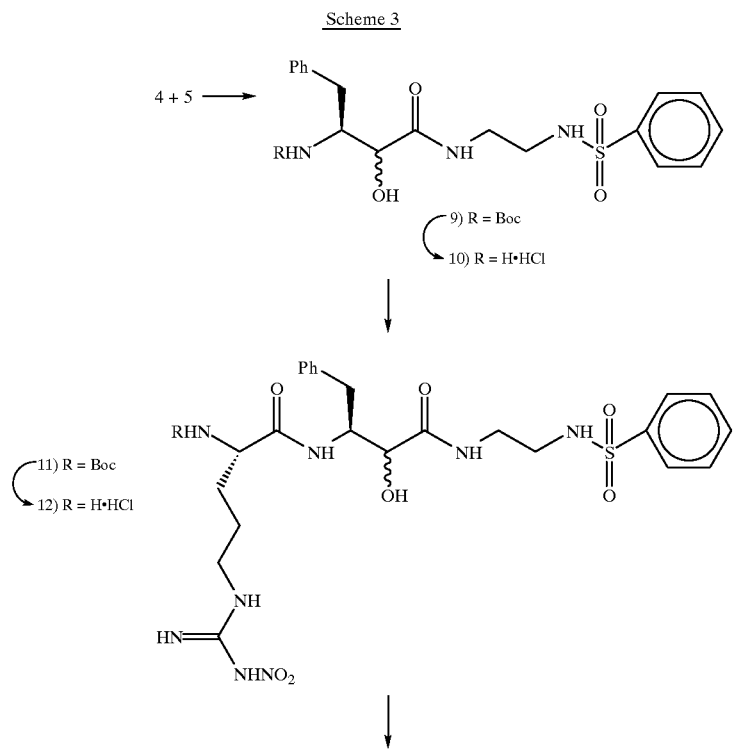

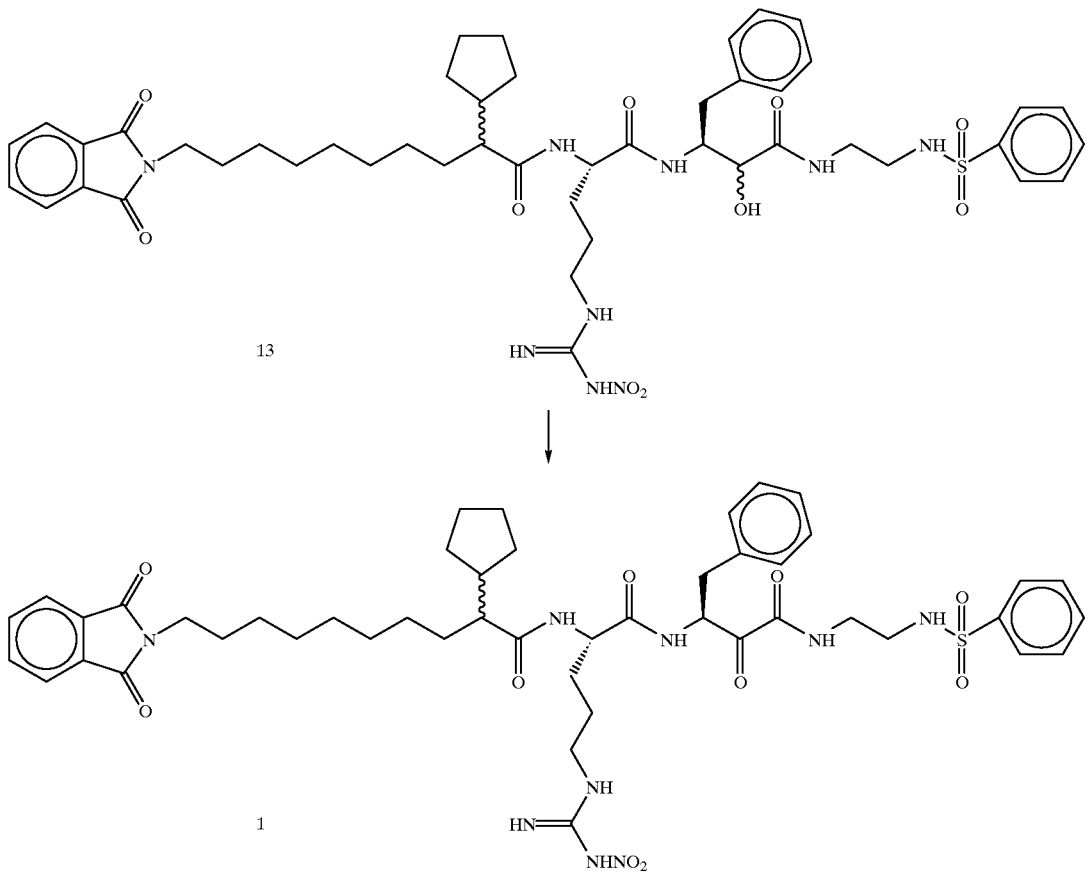

Preparation of Compound 9

To a cooled (0° C.) solution of compound 4 (1.00 g, 0.0034 mol) in anhydrous N,N-dimethylformamide (20 mL) was added N-methylmorpholine (1.40 g, 0.014 mmol) followed by 1-HOBt (0.54 g, 0.0040 mmol) and BOP (1.80 g, 0.0040 mmol). The mixture was stirred for 15 minutes and to it was added compound 5 (0.75g, 0.0032 mmol). The cooling bath was removed and the mixture was stirred for 4 hours, poured into ice-water (200 mL) and extracted into ethyl acetate (3×100 mL). The organic layer was washed with 2% citric acid solution (2×50 mL), 2% sodium bicarbonate solution (2×50 mL), and brine (1×50 mL), and it was dried over anhydrous sodium sulfate. Solvent evaporation under reduced pressure gave a crude material which was washed several times with n-pentane to produce 1.30 g of compound 9.

Compound 9: white solid (diastereomeric mixture); $^1$H-NMR (DMSO-$d_6$) δ 7.90 and 7.65 (2 sets of t, 1H), 7.75 (d, 2H), 7.55 (q, 2H), 7.15 (m, 6H), 6.55 and 5.80 (2 sets of d, 1H), 3.90 (m, 2H), 3.30 (d, 1H), 3.10 (m, 2H), 2.75 (m, 2H), 2.50 (m, 3H), 1.20 (s, 9H). MS m/e 478(M+H), 500(M+Na).

Preparation of Compound 10

To a solution of compound 9 (0.40 g, 0.84 mmol) in 1,4-dioxane (15 mL) was added 4 N HCl in dioxane (15 mL). The reaction mixture was stirred at room temperature for 2 hours and concentrated at reduced pressure to give a residue which was washed several times with ethyl acetate and dried under vacuum to generate 0.30 g of compound 10;

$^1$H-NMR (DMSO-$d_6$) showed complete absence of tBoc peak at δ 1.20 ppm; MS m/e 378 (M+H).

This material was directly used in the next step.

Preparation of Compound 11

This compound was prepared following the same procedure as described before for the synthesis of compound 9. Thus coupling of the compounds 3 (0.074 g, 0.2305 mmol) and 10 (0.100 g, 0.2421 mmol), in the presence of NMM/HOBt/BOP gave 0.117 g of compound 11 (diastereomeric mixture) which was used directly in the next step.

Compound 11: white solid (diastereomeric mixture); $^1$H-NMR (CDCl$_3$) δ 7.85 (d, 2H), 7.50 (m, 3H), 7.20 (m, 5H), 7.40–7.00 (broad, 7H), 6.80 (broad, 1H), 5.50 and 5.10 (2 sets of broad, 1H), 4.50 (broad, 1H), 4.20 (broad, 1H), 3.70–2.80 (a series of m, 8H), 1.65 (s, 9H), 1.60–1.30 (m, 5H). MS m/e 679(M+H), 701(M+Na).

Preparation of Compound 12

This compound was prepared following the same procedure as described before for the synthesis of compound 10. Thus 0.100 g of compound 11 on boc-deprotection by 4 N HCl in dioxane generated 0.088 g of compound 12; $^1$H-NMR (DMSO-$d_6$) showed complete absence of tBoc peak. This material was used directly in the next step.

Preparation of Compound 13

This compound was prepared following the same procedure as described before for the synthesis of compound 9. Thus coupling of the compounds 12 (0.085 g, 0.1383 mmol) and 2 (0.050 g, 0.1297 mmol), in presence of NMM/HOBt/BOP yielded a crude product which was purified by preparative thin layer chromatography (eluant: 4% MeOH in $CH_2Cl_2$) to give 0.050 g of 13 as a diastereomeric mixture.

Compound 13: white solid (diastereomeric mixture); $^1$H-NMR ($CDCl_3$) δ 8.40 (broad, 1H), 8.00–6.80 (a series of m, 20H), 5.40 (broad, 1H), 4.30 and 4.10 (broad, 1H), 3.60 (broad q, 2H), 3.50–2.90 (a series of m, 9H), 2.00–1.00 (a series of m, 29H). MS m/e 946(M+H), 968(M+Na).

Preparation of Compound 1

To a cooled (0° C.) solution of compound 13 (0.045 g, 0.0476 mmol) in anhydrous methylene chloride (4 mL) was added Dess-Martin periodinane reagent (0.040 g, 0.0952 mmol). The cooling bath was removed and the mixture was stirred for an additional 1 hour. It was then diluted with methylene chloride (10 mL), and the solution was washed with 10% sodium thiosulfate solution (5×5 mL), saturated sodium bicarbonate solution (2×5 mL) and brine (1×5 mL). The organic layer was dried over anhydrous sodium sulfate. Solvent removal under reduced pressure gave a residue which was washed with n-pentane (B mL) and dried under vacuum to generate 0.017 g of compound 1.

Compound 1: white solid (diastereomeric mixture); $^1$H-NMR ($CDCl_3$) δ 8.40 (broad, 1H), 8.00–6.80 (a series of m, 20H), 5.50 (broad, 1H), 4.70 (broad, 1H), 3.60 (broad q, 2H), 3.50–2.90 (a series of m, 8H), 2.00–1.00 (a series of m, 28H). MS m/e 944(M+H), 966(M+Na).

Example 2

Preparation of Compound 14

Building blocks used in the synthesis are shown in Scheme 4, below:

above (in Scheme 3) for the synthesis of compound 1. Compound 16 was prepared following the same procedures, as described before (scheme 2) for the synthesis of compound 5, except that 3,4-dichlorobenzenesulfonyl chloride, instead of benzenesulfonyl chloride, was used in an intermediate step.

Compound 14: white solid (diastereomeric mixture); $^1$H-NMR ($CDDl_3$) δ 8.30 (broad, 1H), 7.90 (d, 1H), 7.75 (m, 1H), 7.60 (m, 2H), 7.50 (d, 2H), 7.70–7.20 (a series of broad, 6H), 6.80 (broad, 1H), 5.30 (broad, 1H), 4.70 (broad, 1H), 3.60 (broad t, 2H), 3.35 (broad, 4H), 3.10 (broad, 2H), 2.00–1.00 (a series of m, 31H), 0.90 (q, 6H). MS m/e 978 and 982(M+H with different isotopes of chlorine).

Example 3

Preparation of Compound 17

This compound was assembled from compounds 10 and 18 (Bachem, King of Prussia, Pa.) (see Scheme 5, below) following the same procedures as described previously (in Scheme 3) for the preparation of compound 1, except that the Fmoc group from an intermediate was deprotected by 30% diethylamine in ethyl acetate.

Scheme 4

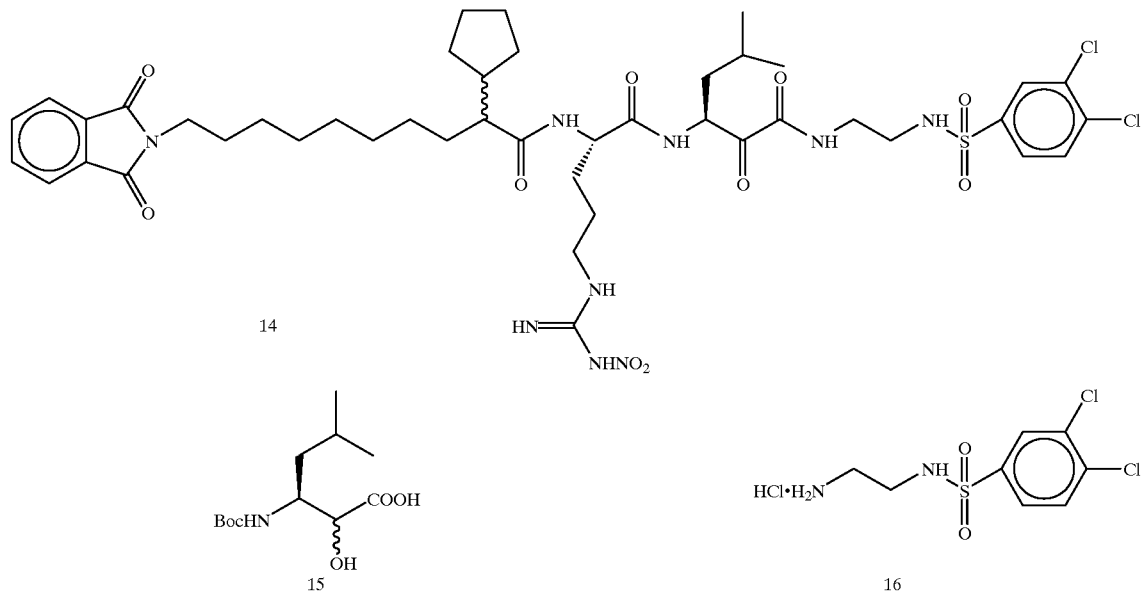

Compound 14 was assembled from the building blocks 2, 3, 15 and 16 following the same procedures as described Scheme 5
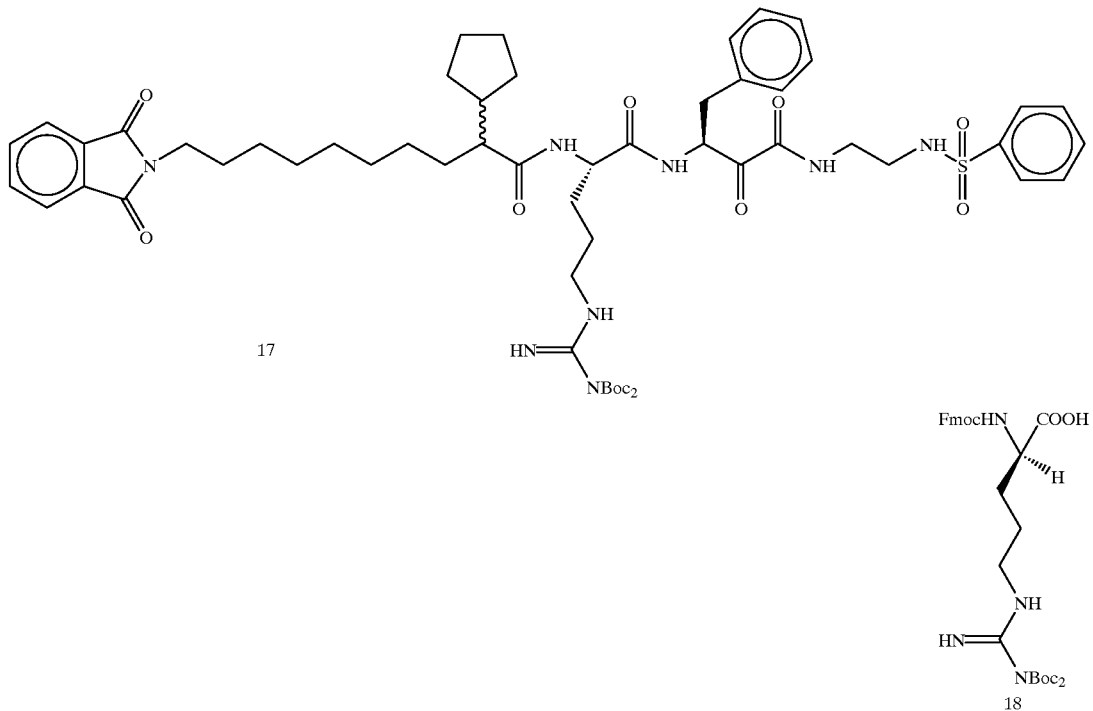
Compound 17: white solid (diastereomeric mixture); $^1$H-NMR (CDCl$_3$) δ 8.35 (broad t, 1H), 7.85 (t, 2H), 7.70 (m, 1H), 7.50 (m, 2H), 7.35–7.05 (m, 11H), 6.90 (t, 1H), 6.50 (d, 1H), 6.00 (t, 1H), 5.20 (t, 1H), 4.50 (broad m, 1H), 3.70 (t, 2H), 3.60–3.00 (m, 8H), 2.00–1.00 (m, 28 H), 1.45 (s, 18H). MS m/e 1099(M+H).
Example 4
Preparation of Compounds 19 and 20
The preparation of compounds 19 and 20 are depicted in Scheme 6, below:
Scheme 6
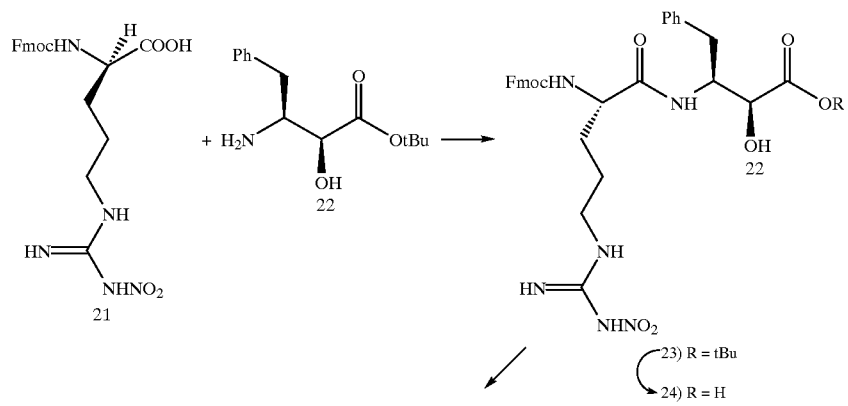

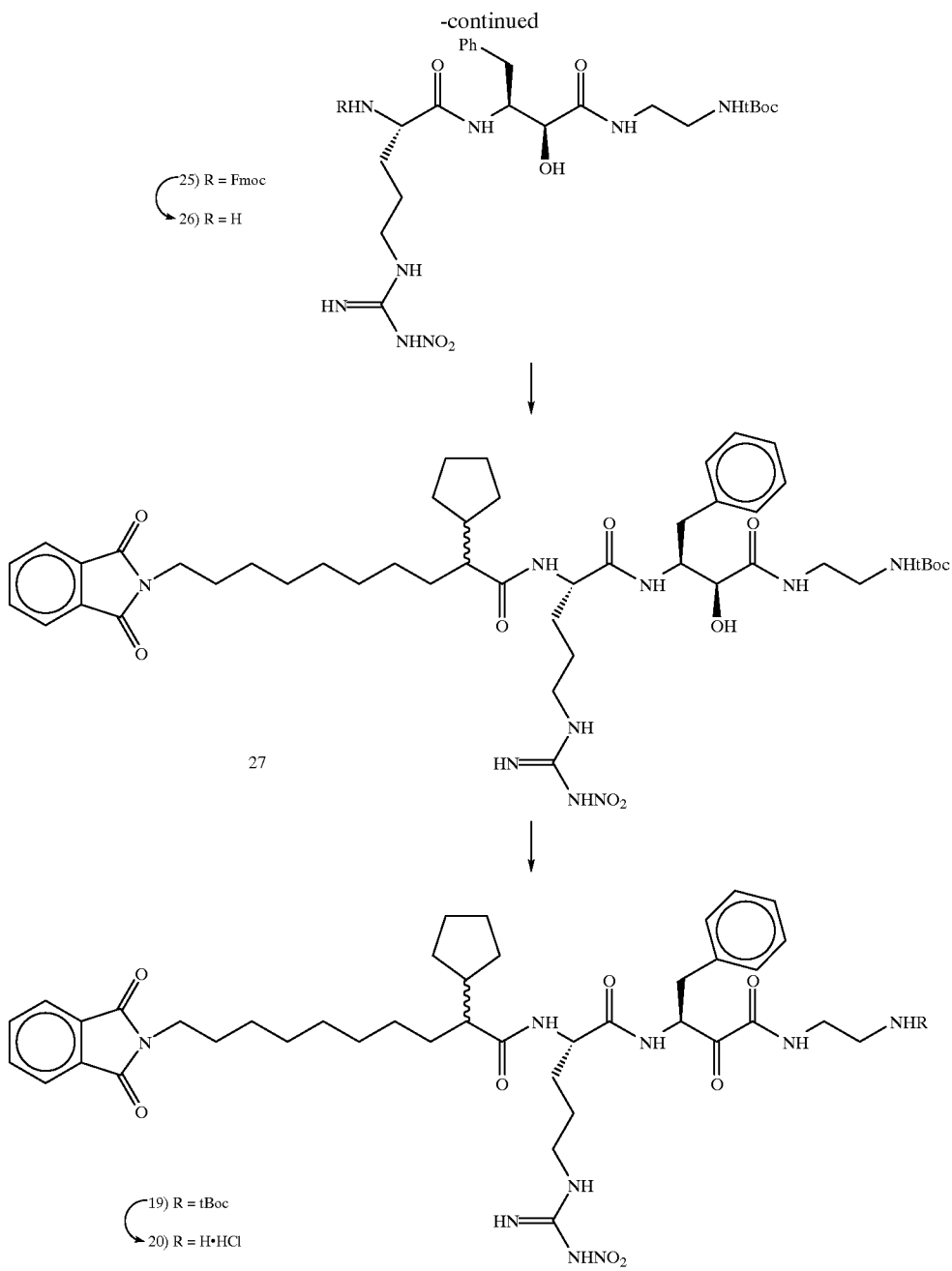

Preparation of Compound 23

This compound was prepared following the same procedure as described before for the synthesis of compound 9. Thus coupling of the compounds 21 (0.532 g, 1.2052 mmol) and 22 (Oxford Asymmetry, Abingdon, UK, 0.334 g, 1.3289 mmol), in the presence of NMM/HOBt/BOP gave 0.810 g of compound 23.

Compound 23: white solid; $R_f$ (TLC, 5% methanol in methylene chloride) 0.43; $^1$H-NMR (CDDl$_3$) δ 8.40 (broad, 1H), 7.75 (d, 2H), 7.55 (d, 2H), 7.40–7.00 (m, 13H), 5.60 (broad d, 1H), 4.60 (broad q, 1H), 4.30 (m, 2H), 4.10 (m, 3H), 3.25 (broad, 2H), 2.90 (broad t, 2H), 2.00–1.20 (m, 5H), 1.30 (s, 9H). MS m/e 675 (M+H), 697 (M+Na)

Preparation of Compound 24

A mixture of compound 23 (0.437 g, 0.6476 mmol), TFA (6 mL), and methylene chloride (6 mL) was stirred at room temperature for 2 hours. The solution was concentrated in vacuo to generate 0.401 g of compound 24 which was used directly in the next step; $^1$H-NMR spectrum of an aliquot showed absence of the tBu peak at δ 1.30 ppm; MS m/e 619(M+H).

Preparation of Compound 25

This compound was synthesized following the same procedure as described before for the synthesis of compound 9. Thus coupling of compounds 24 (0.397 g, 0.6417 mmol) and 7 (0.113 g, 0.7053 mmol), in the presence of NMM/HOBt/BOP produced 0.340 g of compound 25; MS m/e 660(M-tBoc), 761(M+H), 783(M+Na). This material was used directly in the next step.

Preparation of Compound 26

A mixture of compound 25 (0.320 g, 0.4206 mmol) and 30% diethylamine in ethyl acetate (6 mL) was stirred at room temperature for 1 hour. TLC showed complete disappearance of the starting material. The reaction mixture was concentrated in vacuo to generate a residue which was washed several times with pet ether to produce 0.226 g of compound 26 which was directly used in the next step.

Preparation of Compound 27

This compound was prepared following the same procedure as described before for the synthesis of compound 9. Thus coupling of the compounds 2 (0.162 g, 0.042 mmol) and 26 (0.226 g, 0.042 mmol), in the presence of NMM/HOBt/BOP produced a crude product which was purified by preparative thin layer chromatography (eluant: 8% MeOH in $CH_2Cl_2$) to give 0.040 g of compound 27.

Compound 27: white solid (diastereomeric mixture); $^1$H-NMR (CDCl$_3$) δ 8.40 (broad, 1H), 7.80 (m, 2H), 7.70 (m, 2H), 7.60–7.00 (m, 10H), 6.70 (broad, 1H), 4.50 (broad, 2H), 4.10 (broad, 1H), 3.70 (t, 2H), 3.50–3.00 (a series of m, 8H), 2.00–1.00 (a series of m, 29H), 1.40 (s, 9H). MS m/e 806(M+H-tBoc), 906(M+H), 928(M+Na).

Preparation of Compound 19

This compound was prepared following the same procedure as described above (Scheme 3) for the synthesis of compound 1. Thus Dess-Martin oxidation of 0.035 g of compound 27 produced 0.023 g of compound 19.

Compound 19: white solid (diastereomeric mixture); $^1$H-NMR (CDDl$_3$) δ 8.40 (broad, 1H), 8.00–7.00 (a series of m, 14H), 6.80 (broad, 1H), 5.50 and 5.30 (2 sets of broad, 1H), 4.60 (broad, 1H), 3.70 (t, 2H), 3.50–3.10 (a series of m, 7H), 3.00 (m, 1H), 2.00–1.00 (a series of m, 28H), 1.40 (s, 9H). MS m/e 926(M+Na), 942(M+K)

Preparation of Compound 20

Compound 19 (0.018 g), on tBoc-deprotection (4 N HCl in dioxane, room temp), gave compound 20 (0.015 g).

Compound 20: white solid (diastereomeric mixture); $^1$H-NMR (DMSO-d$_6$) δ 8.60 (broad, 1H), 8.40 (broad, 1H), 8.20 (broad, 1H), 8.00–7.00 (a series of m, 15H), 5.20 (broad, 1H), 4.20 (broad, 2H), 3.70–2.70 (a series of m, 9H), 2.00–0.90 (a series of m, 28H). MS m/e 804(M+H).

Preparation of Compound 28

The preparation of compound 28 is shown in Scheme 7, below:

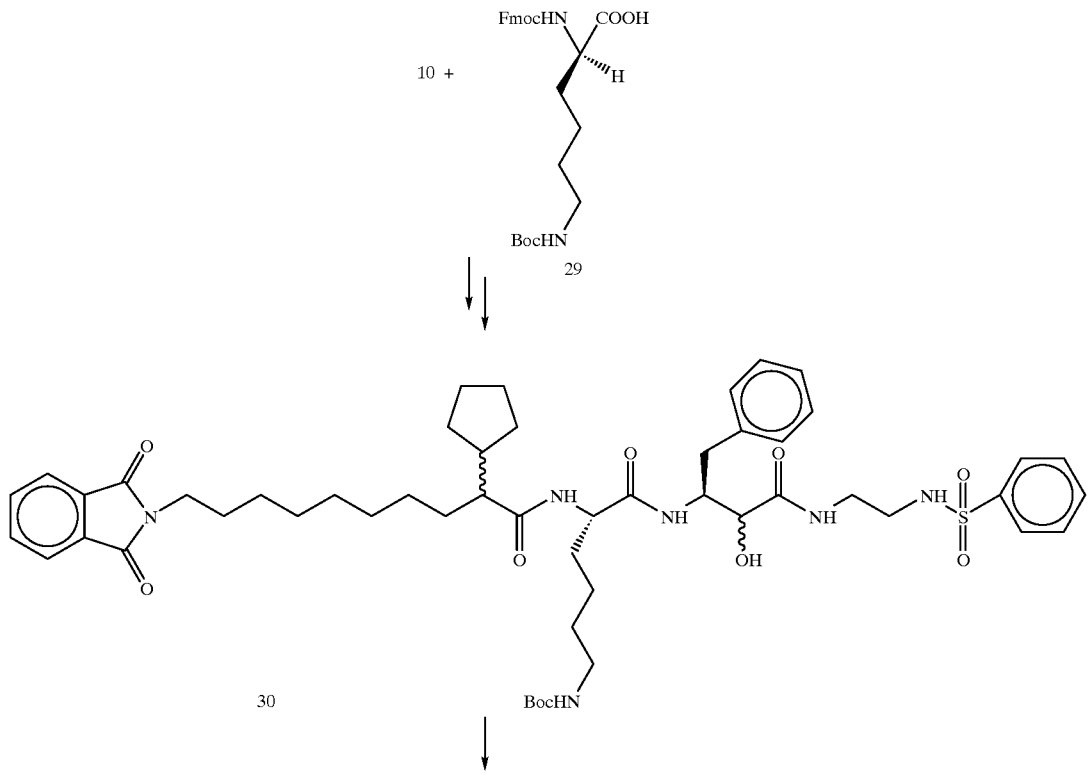

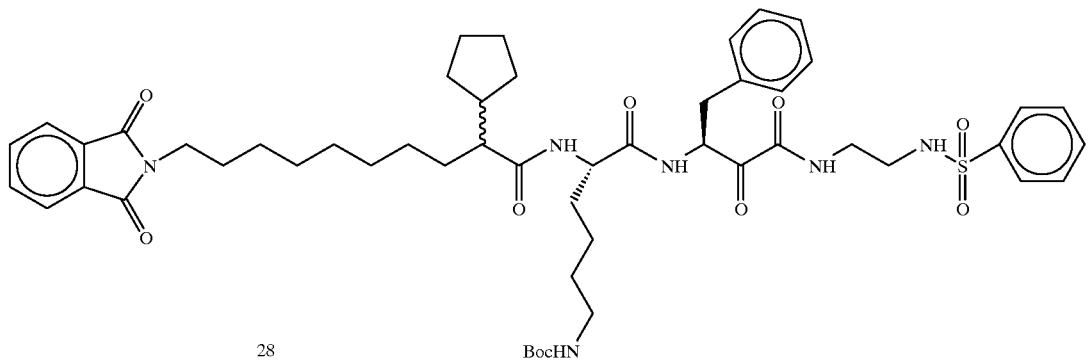

Compound 28 was prepared from intermediate compound 30 which in turn was prepared from the compounds 10 and 29 (STAR Biochemicals, Torrance, Calif.) following the same general procedures, as described above (Scheme 3), except that the Fmoc group from one of the intermediates was deprotected by 30% diethylamine in ethyl acetate.

Compound 28: white solid (diastereomeric mixture); $^1$H-NMR (CDCl$_3$) δ 7.80 (d, 2H), 7.70 (m, 0H), 7.50 (m, 2H), 7.40–7.00 (m, 10H), 6.40 (broad d, 1H), 6.20 (broad d, 1H), 5.40 (broad d, 1H), 5.20 (broad d, 1H), 4.80 (broad d, 0 H), 4.50 (broad, 1H), 3.65 (t, 2H), 3.40 (broad, 2H), 3.30–2.90 (broad m, 6H), 2.00–1.00 (m, 30H), 1.60 (s, 9H). MS m/e 871(M+H−tBoc), 971(M+H), 993(M+Na).

Example 6

Preparation of Compounds 34 and 35

The preparation of compounds 34 and 35 is shown in Scheme 8:

Scheme 8

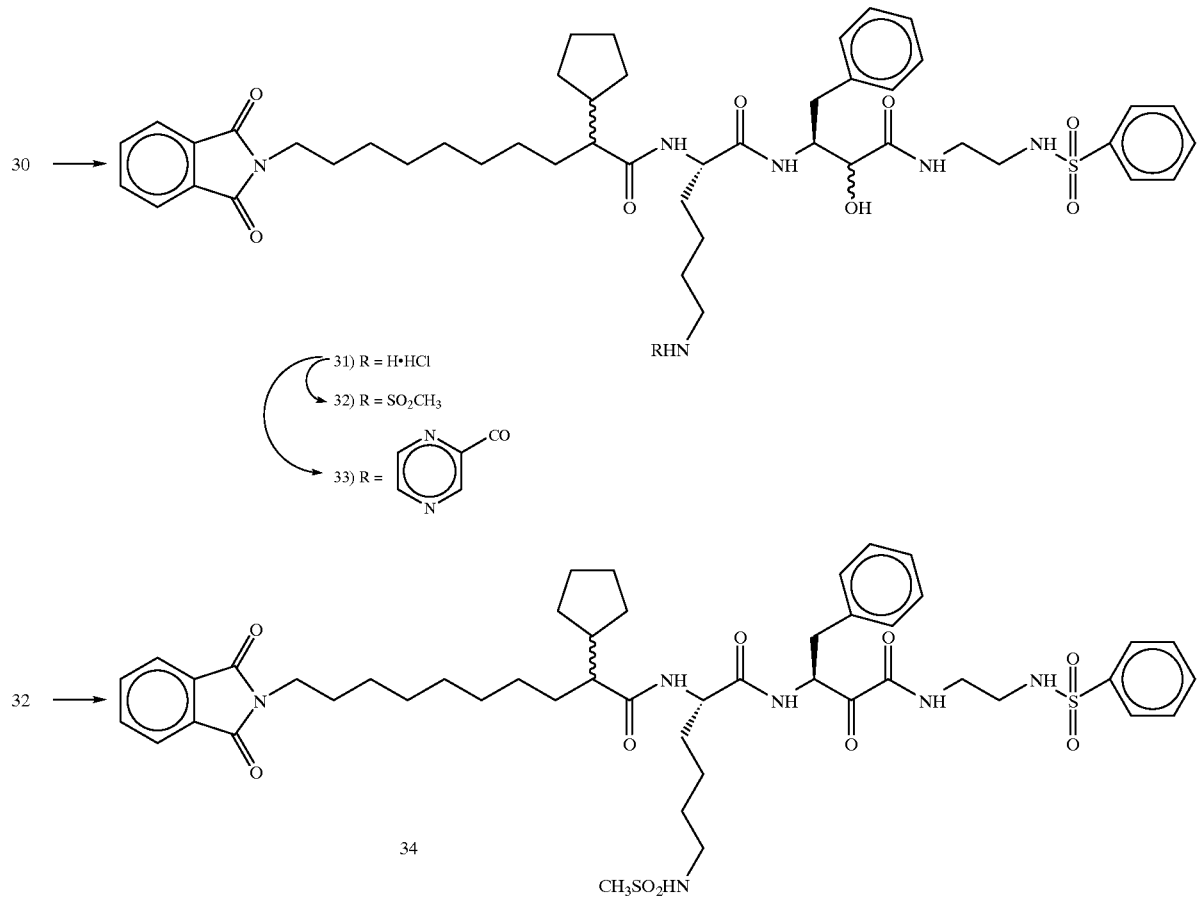

-continued

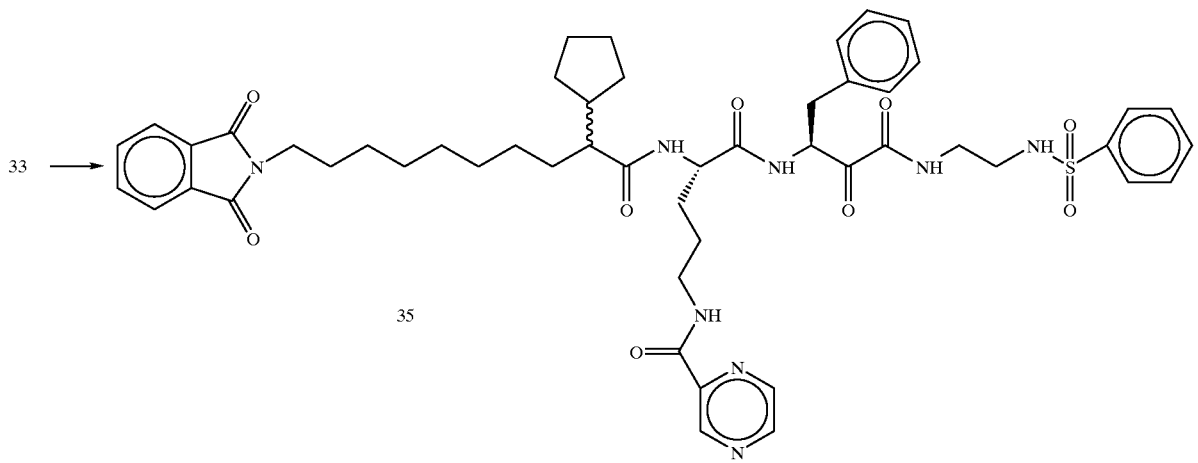

35

Preparation of Compound 34

Compound 30 was deprotected (4 N HCl in dioxane, room temp, 1 hour) as described above (in Scheme 3) to generate the amine salt 31 which was sulfonylated (Et$_3$N, CH$_3$SO$_2$Cl, CH$_2$Cl$_2$, 0° C. to room temp, 0.5 hour) as described above (Scheme 2) to produce compound 32. Dess-Martin oxidation of compound 32 generated compound 34.

Compound 34: white solid (diastereomeric mixture); $^1$H-NMR (CDCl$_3$) δ 7.80 (d, 2H), 7.70 (m, 1H), 7.55 (m, 2H), 7.40–7.00 (m, 10H), 6.80 (m, 1H), 6.40 (d, 1H), 6.00 (broad d, 1H), 5.40 (broad, 1H), 5.20 (2 sets of broad t, 1H), 4.50 (broad d, 1H), 3.65 (t, 2H), 3.40 (broad, 2H), 3.30–3.00 (broad m, 6H), 2.90 (d, 3H), 2.00–1.00 (m, 30H). MS m/e 949 (M+H), 971 (M+Na), 987 (M+K)

Preparation of Compound 35

The amine salt, compound 31, was carbonylated (pyrazine-2-carboxylic acid, NMM, HOBt, BOP, DMF, 0° C. to room temp, 1 hour), as described above in Scheme 3 to produce compound 33. Dess-Martin oxidation of compound 33 generated compound 35.

Compound 35: white solid (diastereomeric mixture); $^1$H-NMR (CDCl$_3$) δ 9.35 (s, 1H), 8.70 (s, 1H), 8.50 (s, 1H), 8.00 (2 sets of broad t, 1H), 7.80–7.00 (m, 16H), 6.70 (t, 1H), 6.50 (broad d, 1H), 5.40 (broad, 1H), 4.60 (broad, 1H), t, 1H), 3.65 (m, 2H), 3.40 (broad, 2H), 3.30–2.80 (m, 6H), 2.00–1.00 (m, 30H). MS m/e 977(M+H), 999 (M+Na), 1015(M+K).

Example 7

Preparation of Compounds 36 and 37

The preparation of compounds 36 and 37 is shown below in Scheme 9:

Scheme 9

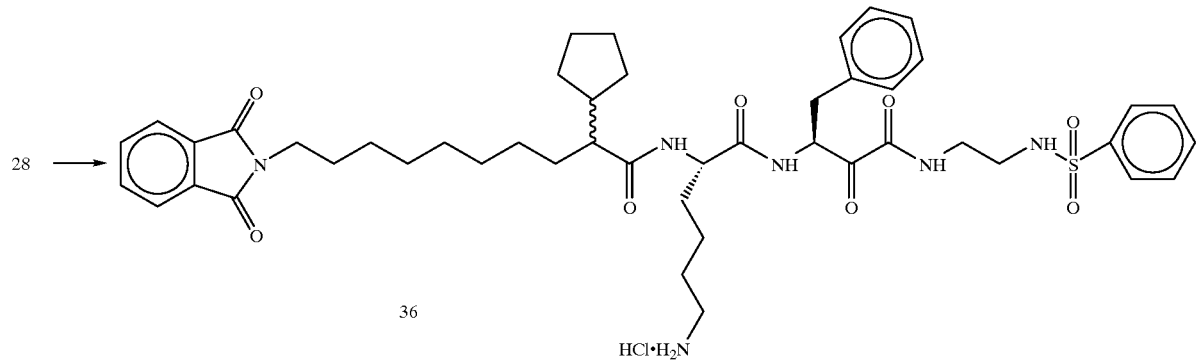

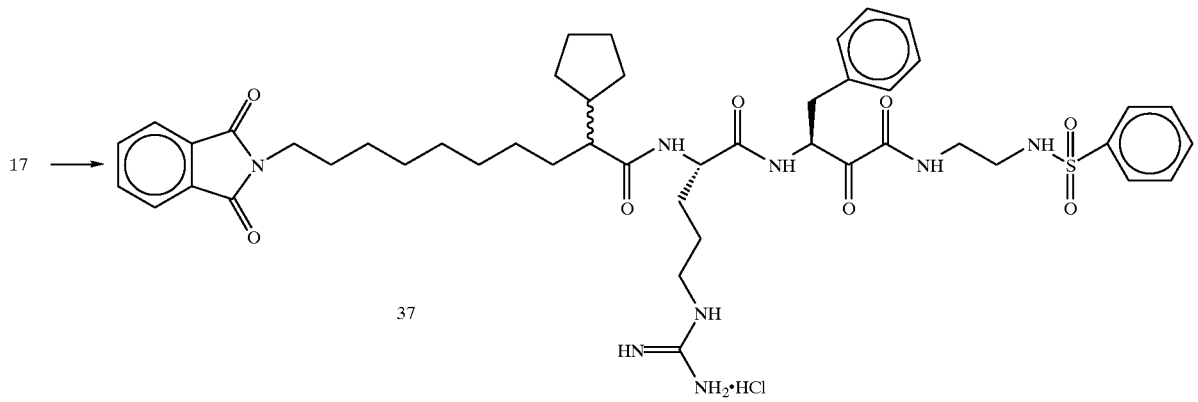

Preparation of Compound 36
Compound 28 (0.052 g) on tBoc-deprotection (4 N HCl in dioxane, room temp) generated compound 36 (0.041 g).
Compound 36: white solid (diastereomeric mixture); $^1$H-NMR (DMSO-$d_6$) δ 8.65 (broad, 1H), 8.20 (broad, 1H), 7.80 (broad, 10H) t 7.60 (broad, 3H), 7.15 (broad, 5H), 5.20 (broad, 1H), 4.25 (broad, 1H), 3.60–2.60 (a series of broad m, 11H), 2.00–0.80 (m, 30H). MS m/e 871(M+H).
Preparation of Compound 37
Compound 17 (0.034 g) on tBoc-deprotection (4 N HCl in dioxane, room temp, overnight) yielded compound 36 (0.020
Compound 37: white solid (diastereomeric mixture); $^1$H-NMR (DMSO-$d_6$) shows absence of tBoc groups; MS m/e 899(M+H).

Example 8
Preparation of Compounds 38 and 39

Compounds 38 and 39 were synthesized from appropriate starting materials following the procedures described above.
Compound 38: white solid (diastereomeric mixture); $^1$H-NMR (CDDl$_3$) δ 8.00–6.80 (a series of m, 20H), 5.60 (broad, 1H), 4.60 (broad, 1H), 3.60 (t, 2H), 3.50–2.90 (a series of m, 8H), 2.80 (s, 3H), 2.00–1.00 (a series of m, 28H). MS m/e 958 (M+H), 980 (M+Na).
Compound 39: white solid (diastereomeric mixture); $^1$H-NMR (CDCl$_3$) spectrum is a complex one due to the presence of two isomers. MS m/e 872 (M+H).

Example 9
Assay for Chymotrypsin-like Activity of MCP
The chymotrypsin-like catalytic activity of the 20S form of MCP was measured using enzyme which was isolated in a latent state from human liver, as described in U.S. Pat. No. 5,614,649, which is hereby incorporated by reference in its entirety.

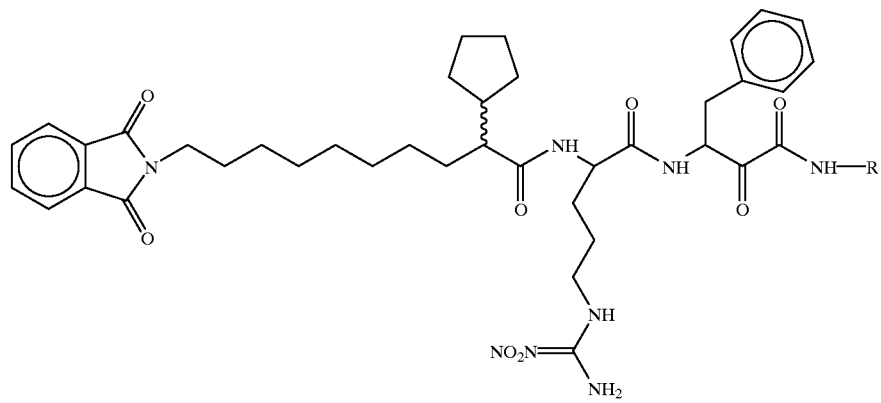

| Compound No. | R |
|---|---|
| 38 | —(CH$_2$)$_2$NMeSO$_2$Ph |
| 39 | 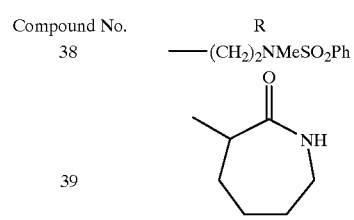 |

Aliquots (5 uL) of inhibitors dissolved in DMSO were dispensed into a 96-well plate in triplicate. The MCP was diluted into activation buffer (20 mM Tris (pH 7.5), 0.04% SDS), 85 uL aliquots of diluted enzyme were added to the inhibitor-containing wells, and the mixtures were incubated for 15 minutes at 27° C. Reactions were initiated by the addition of 10 uL of Suc-LLVY-AMC (final concentration of 100 uM), and product formation was monitored over 20 minutes at 1.5 minute intervals using a Cytofluor Series 4000 plate-reading fluorimeter ($\lambda_{ex}$=360 nm; $\lambda_{em}$=460 nm). Substrate hydrolysis in the absence of inhibitor was linear over the entire duration of the assay.

Inhibition of MCP chymotrypsin-like activity was calculated as the percent decrease in the rate of substrate hydrolysis in the presence of inhibitor relative to the rate in its absence. The $IC_{50}$ values for inhibitors (corresponding to the concentration of inhibitor yielding 50% inhibition) were determined from the percent decrease in rates of substrate hydrolysis in the presence of seven concentrations of test compound. The results were plotted as percent inhibition versus log inhibitor concentration, and the $IC_{50}$ was calculated by fitting the data to the four-parameter logistic equation shown below using the program GraphPad Prism (GraphPad Software, Inc., San Diego, Calif.)

$$y=d+[(a-d)/(1+x/c)b)]$$

The parameters a, b, c, and d are defined as follows: a is % inhibition in the absence of inhibitor, b is the slope, c is the ICE, and d is the % inhibition at an infinite concentration of inhibitor.

Results are summarized in Table I which lists examples of the invention.

TABLE 1

Inhibition of MCP by Compounds of the Invention

| Compound No. | $IC_{50}$ nM |
|---|---|
| 1 | 2 |
| 14 | 9 |
| 17 | 34% @ 100 nM |
| 19 | 4 |
| 20 | 117 |
| 28 | 48% @ 1000 nM |
| 34 | 71 |
| 35 | 139 |
| 36 | 39 |
| 37 | 31% @ 100 nM |
| 38 | 19 |
| 39 | 5 |

Example 10
In Vivo Anti-tumor Activity of Compound 1 a. Materials: Compound 1 used for in vivo studies was formulated in 25% Solutol.

b. Cell line: The murine melanoma cell line, B16-F0, was grown at 37° C. in a humidified incubator, with a 95% air/5% $CO_2$ atmosphere, in Dulbecco's modified Eagle's medium with 4.5 g/l glucose (Cellgro/Mediatech, Washington, D.C.) containing 10% fetal bovine serum (Hyclone Labs, Logan, Utah), 2 mM glutamine (GibcoBRL, Long Island, N.Y.), penicillin (100 I.U./mL) (GibcoBRL), and streptomycin (100 μg/mL) (GibcoBRL). The cells were determined to be free of mycoplasma and rodent viruses (MAP testing). Exponentially growing cells were harvested using 5 mL of warm trypsin/EDTA (0.05%, 0.5 mM) (GibcoBRL). The total volume was brought up to 10 mL with Complete Medium to neutralize trypsin and cells were counted with a hemocytometer. The cells were then collected by brief centrifugation and the cell pellet was resuspended in Phosphate Buffered Saline (GibcoBRL) to achieve the final concentration of 1×107 live cells/ml.

c. Animals: Female C57BL mice (20–25 g) obtained from Harlan Sprague Dawley, Indianapolis, IN were maintained five mice/cage and given a commercial diet and water ad libitum. Animals were housed under humidity- and temperature-controlled conditions and light/dark cycle was set at 12-hour intervals. Mice were quarantined for one week before experimental manipulation.

d. Tumor cell implantation and growth: Exponentially growing B16-F0 cells, cultured as described above, were harvested and injected (1×10$^6$ cells/mouse) into the right flank of the mice. Fifty (50) animals bearing tumors of 0.01–0.3 cm$^3$ size were divided into 5 groups of 10 animals each. Compound 1 was administered at 10 mg/kg/day, ip; Vehicle (25% Solutol) was administered at 1 ml/kg/day, ip.

e. Tumor measurements: Tumors were measured using a vernier caliper every 2 to 3 days. Tumor volume was calculated using the formula:

$$V(cm)^3 = 0.5236 \times length(cm) \times width(cm) \ [(length(cm)+width(cm))/2].$$

Results from the in vivo study are presented in FIG. 1, wherein "x" represents p<0.05; "xx" represents p<0.01; and "xxx" represents p<0.001, all relative to vehicle control by Newman-Keols test.

The results show the effectiveness of Compound 1 in reducing tumor volume.

It is intended that each of the patents, applications, and printed publications mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound having the Formula I:

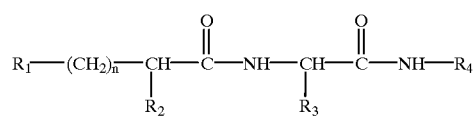

wherein:
R$_1$ is selected from the group consisting of —C—N, —C(=O)OR$_8$, phthalimido, —NHSO$_2$R$_8$, and —NH—J;

R$_2$ is selected from the group consisting of H, hydroxyl, alkyl having from one to ten carbons and cycloalkyl having from three to seven carbons;

R$_3$ is selected from the group consisting of —(CH$_2$)$_m$— NHC(=N—R$_5$)—NH$_2$, —R$_6$—H, —R$_6$—J, —R$_{12}$— (J)$_2$, —R$_6$—NO, —R—CN, —(CH$_2$)$_m$—NH$_2$, and —(CH$_2$)—NH—J;

$R_4$ is —CH(CH$_2$R$_7$)—Q;

$R_5$ is selected from the group consisting of -NO$_2$, —CN, and —J;

$R_6$ is —(CH$_2$)$_m$—NH—C(=NH)—NH—;

$R_{12}$ is —(CH$_2$)$_m$—NH—C(=NH)—N—;

Q is —C(=O)C(=O)NH—X—A—Y;

$R_7$ is selected from the group consisting of phenyl, and alkyl having from one to eight carbons, said alkyl group being optionally substituted with one or more halogen atoms, aryl, or heteroaryl groups;

$R_8$ is selected from the group consisting of hydrogen and alkyl having from one to six carbons, said alkyl group being optionally substituted with one or more halogen atoms, aryl or heteroaryl groups;

X is a bond or —O—;

A is an alkylene group of 1 to 8 carbons, said alkylene group being optionally substituted with one or more halogen atoms, aryl, or heteroaryl groups;

Y is N(R$_{13}$)—G;

G is selected from the group consisting of H, a blocking group, SO$_2$R$_9$, —C(=O)NHR$_{10}$, —C(=S)NHR$_{10}$, and —CO$_2$R$_9$;

or the moiety —A—Y forms a 5-, 6-, or 7-membered lactam ring;

$R_9$ is selected from the group consisting of alkyl, aryl, and heteroaryl, said alkyl, aryl, or heteroaryl groups being optionally substituted with K;

$R_{10}$ is selected from the group consisting of H, alkyl, aryl, and heteroaryl, said alkyl, aryl, or heteroaryl groups being optionally substituted with K;

$R_{13}$ is selected from the group consisting of H and lower alkyl;

J is a blocking group;

K is selected from the group consisting of halogen, CO$_2$R$_{10}$, R$_{10}$OC(=O), R$_{10}$OC(=O)NH, OH, CN, NO$_2$, NR$_{10}$R$_{11}$, N=C(NR$_{10}$R$_{11}$)$_2$, SR$_{10}$, OR$_{10}$, phenyl, naphthyl, heteroaryl, and a cycloalkyl group having from 3 to 8 carbon atoms;

$R_{11}$ is the same as $R_{10}$;

n is an integer from 5 to 10;

m is an integer from 2 to 5;

or a pharmaceutically acceptable salt thereof; with the proviso that when X is a bond and $R_3$ is —R$_6$—H or —(CH$_2$)$_m$—NH$_2$, then G is SO$_2$R$_9$.

2. The compound of claim 1 wherein R, is phthalimido, —C≡N, —C(=O)OCH$_3$, or —NHSO$_2$CF$_3$.

3. The compound of claim 1 wherein $R_2$ is H or cyclopentyl.

4. The compound of claim 1 wherein $R_3$ is —R$_6$—J, —R$_6$—NO$_2$, —R$_6$—H, —R$_{12}$—(J)$_2$, —(CH$_2$)$_m$—NH—J, or —(CH)$_m$—NH$_2$.

5. The compound of claim 4 wherein J is Boc, ethylsulfonyl or pyrazinoyl.

6. The compound of claim 1 wherein $R_7$ is phenyl or lower alkyl.

7. The compound of claim 6 wherein $R_7$ is isopropyl.

8. The compound of claim 1 wherein X is a bond.

9. The compound of claim 1 wherein A is —CH$_2$CH$_2$.

10. The compound of claim 1 wherein G is SO$_2$-aryl.

11. The compound of claim 1 wherein G is SO$_2$-aryl, said aryl group being substituted with one or more halogen atoms.

12. The compound of claim 10 wherein G is SO$_2$-phenyl.

13. The compound of claim 11 wherein G is SO$_2$-phenyl, said phenyl group being substituted with one or more halogen atoms.

14. The compound of claim 1 wherein G is H or a blocking group.

15. The compound of claim 14 wherein said blocking gorup is t-Boc.

16. The compound of claim 1 wherein X is a bond, A is —CH$_2$CH$_2$—, n is 8, $R_1$ is phthalimido, $R_2$ is cycloalkyl, G is H, t-Boc or SO$_2$R$_9$ where R$_9$ is phenyl optionally subsituted with halogen, $R_7$ is phenyl or alkyl, and $R_3$ is —(CH)$_m$—NHC(=NH)—NO$_2$, —(CH$_2$)$_m$—NHC(=NH)—N(Boc)$_2$, —(CH$_2$)$_m$—NHC(=NH)—NH$_3$Cl, (CH$_2$)$_m$—NH$_3$Cl, or —(CH$_2$)$_m$—NH—J where J is Boc, methylsulfonyl or pyrazinoyl.

17. The compund of claim 16 wherein $R_2$ is cyclopentyl, and $R_7$ is isopropyl.

18. The compound of claim 1 wherein $R_1$ is N-phthalimido, $R_2$ is cyclopentyl, $R_7$ is phenyl or isopropyl, X is a bond, A is —CH$_2$—CH$_2$—, and Y is —NH—SO$_2$Ph, —NH—SO$_2$—(3,4-dichloro)Ph, —NH—tBoc, NH$_2$HCl, N(Me)SO$_2$Ph, or the moiety —A—Y forms the structure:

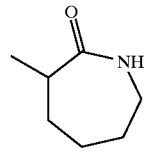

and $R_3$ is —(CH$_2$)$_3$—NH—C(=NH)—NHNO$_2$, —(CH$_2$)$_3$—NH—C(=NH)—NBoc$_2$, —(CH$_2$)$_4$—NH—Boc, —(CH$_2$)$_4$—NH—SO$_2$CH$_3$, —(CH$_2$)$_3$—NH-pyrazinoyl, —(CH$_2$)$_4$—NH$_2$HCl, —(CH$_2$)$_3$—NH—C(=NH)—NH$_2$HCl, or —(CH$_2$)$_3$—NH—C(=NNO$_2$)—NH$_2$.

19. The compound of claim 1 wherein $R_1$ is N-phthalimido, $R_2$ is cyclopentyl, and $R_3$ and $R_4$ are selected in accordance with the following table:

| $R_3$ is: |
| --- |
| —(CH$_2$)$_3$—NH—C(=NH)—NHNO$_2$ |
| —(CH$_2$)$_3$—NH—C(=NH)—NHNO$_2$ |
| —(CH$_2$)$_3$—NH—C(=NH)—NBoc$_2$ |
| —(CH$_2$)$_3$—NH—C(=NH)—NHNO$_2$ |
| —(CH$_2$)$_3$—NH—C(=NH)—NHNO$_2$ |
| —(CH$_2$)$_4$—NH-Boc |
| —(CH$_2$)$_4$—NH—SO$_2$CH$_3$ |
| —(CH$_2$)$_3$—NH-pyrazinoyl |
| —(CH$_2$)$_4$—NH$_2$·HCl |
| —(CH$_2$)$_3$—NH—C(=NH)—NH$_2$·HCl |
| —(CH$_2$)$_3$—NH—C(=NNO$_2$)—NH$_2$ |
| —(CH$_2$)$_3$—NH—C(=NNO$_2$)—NH$_2$ |

-continued and R₄ is:

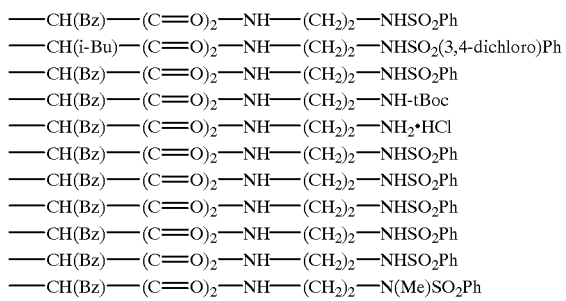

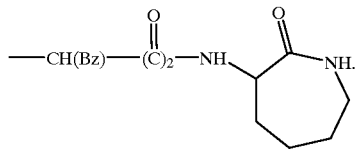

20. A composition for inhibiting multicatalytic protease comprising a compound of claim 1 and a pharmaceutically acceptable carrier.

21. A composition for decreasing the loss of muscle mass comprising a compound of claim 1 and a pharmaceutically acceptable carrier.

22. A composition for the treatment of muscle wasting disorders comprising a compound of claim 1 and a pharmaceutically acceptable carrier.

23. A composition of claim 22 wherein the disorder is a muscular dystrophy, cardiac cachexia, emphysema, diabetes, leprosy, malnutrition, osteomalacia or cancer cachexia.

24. A composition for the reduction of Cu/Zn superoxide dismutase-1 enzyme degradation comprising an inhibitor of multicatalytic protease and a pharmaceutically acceptable carrier.

25. A composition for the treatment of a disorder characterized by a reduction in Cu/Zn superoxide dismutase-1 enzyme activity comprising a compound of claim 1 and a pharmaceutically acceptable carrier.

26. The composition of claim 25 wherein the disorder is amyotrophic lateral sclerosis, Parkinson's disease, Alzheimers's disease, Huntington's disease, stroke, trauma, or ischemia.

27. A method for inhibiting multicatalytic protease comprising contacting a multicatalytic protease with an inihibitory amount of a compound of claim 1.

28. A method for decreasing the loss of muscle mass comprising administering to a patient a therapeutically effective amount of a compound of claim 1.

29. A method for the treatment of muscle wasting disorders comprising administering to a patient a therapeutically effective amount of a compound of claim 1.

30. The method of claim 29 wherein said disorder is muscular dystrophy, cardiac cachexia, emphysema, diabetes, leprosy, malnutrition, osteomalacia or cancer cachexia.

31. A method for reducing the degradation of Cu/Zn superoxide dismutase-1 enzyme in a mammal wherein said degradation is associated with a disease or disorder caused by said degredation comprising administering to a patient a therapeutically effective amount of a compound of claim 1.

32. A method for the treatment of disorders characterized by a reduction in Cu/Zn superoxide dismutase-1 enzyme activity comprising administering to a patient a compound of claim 1.

* * * * *

UNITED STATES PATENT AND TRADEMARK OFFICE
CERTIFICATE OF CORRECTION

PATENT NO.     : 6,310,057 B1
DATED          : October 30, 2001
INVENTOR(S)    : Chatterjee et al.

It is certified that error appears in the above-identified patent and that said Letters Patent is hereby corrected as shown below:

Title page,
Item [56], References Cited, OTHER PUBLICATIONS, "Bowling, A.C. et al.," reference, please delete "Scelerosis" and insert -- Sclerosis -- therefor.

Column 3,
Line 19, please delete "factor a" and insert -- factor α -- therefor.

Column 5,
Line 16, please delete "–COORS" and insert -- –$CO_2R_9$ -- therefor.

Column 6,
Line 60, following "FIG. 1", please delete "is".

Column 7,
Line 20, please delete "–$(CH_2)_m$–$NH_7$" and insert -- –$(CH_2)_m$–$NH_2$ -- therefor.
Line 58, please delete "$R_{10}C(=O)$, $R_{10}C(=O)NH$," and insert -- $R_{10}OC(=O)$, $R_{10}OC(=O)NH$, -- therefor.

Column 8,
Line 4, please delete "reacemates" and insert -- racemates -- therefor.
Line 25, please delete "havoing" and insert -- having -- therefor.
Line 49, please delete "0, N or S" and insert -- O, N or S -- therefor.

Column 14,
Line 59, please delete "a-hydroxy" and insert -- α-hydroxy -- therefor.

Column 15,
Line 20, please delete "pH~S-6" and insert -- pH~5-6 -- therefor.
Line 28, please delete "($CDDl_3$)" and insert -- ($CDCl_3$) -- therefor.

Column 19,
Line 20, please delete "(B mL)" and insert -- (8 mL) -- therefor.

Column 20,
Line 11, please delete "($CDDl_3$)" and insert -- ($CDCl_3$) -- therefor.

Column 23,
Line 62, please delete "($CDDl_3$)" and insert -- ($CDCl_3$) -- therefor.

UNITED STATES PATENT AND TRADEMARK OFFICE
CERTIFICATE OF CORRECTION

PATENT NO.    : 6,310,057 B1
DATED         : October 30, 2001
INVENTOR(S)   : Chatterjee et al.

It is certified that error appears in the above-identified patent and that said Letters Patent is hereby corrected as shown below:

Column 26,
Line 7, "($CDDl_3$)" and insert -- ($CDCl_3$) -- therefor.

Column 27,
Line 26, please delete "(m, 0H)" and insert -- (m, 1H) -- therefor.

Column 28,
Line 19, please delete "0 H)" and insert -- 1H) -- therefor.

Column 31,
Line 24, please delete "($DMSQ$-$d_6$)" and insert -- ($DMSO$-$d_6$) -- therefor.
Line 25, please delete "(broad, 10H) t 7.60" and insert -- (broad, 10H) 7.60 -- therefor.

Column 32,
Line 23, please delete "($CDDl_3$)" and insert -- ($CDCl_3$) -- therefor.

Column 33,
Line 27, please delete "$y=d+[(a-d)/(1+x/c)b)]$" and insert -- $y=d+[(a-d)/(1+x/c)^b)]$ -- therefor.
Line 31, please delete "ICE" and insert -- $IC_{50}$ -- therefor.

Column 34,
Line 9, please delete "1x107" and insert -- $1x10^7$ -- therefor.
Line 58, please delete "–C–N," and insert -- –C≡N, -- therefor.
Line 66, please delete "–$R_6$–NO, –R–CN," and insert -- –$R_6$–$NO_2$, –$R_6$–CN, -- therefor.
Line 67, please delete "–($CH_2$)–NH–J" and insert -- –($CH_2$)$_m$–NH–J -- therefor.

Column 35,
Line 48, please delete "wherein R," and insert -- wherein $R_1$ -- therefor.
Lines 56-57, please delete "ethylsulfonyl" and insert -- methylsulfonyl -- therefor.
Line 62, please delete "–$CH_2CH_2$." and insert -- $CH_2CH_2$–. -- therefor.

UNITED STATES PATENT AND TRADEMARK OFFICE
CERTIFICATE OF CORRECTION

PATENT NO. : 6,310,057 B1
DATED : October 30, 2001
INVENTOR(S) : Chatterjee et al.

It is certified that error appears in the above-identified patent and that said Letters Patent is hereby corrected as shown below:

Column 36,
Line 18, please delete "–(CH)$_m$–NHC–(=NH)–NO$_2$," and insert -- –(CH$_2$)$_m$–NHC–(=NH)–NO$_2$, -- therefor.
Line 20, please delete "(CH$_2$)$_m$–NH$_3$Cl," and insert -- –(CH$_2$)$_m$–NH$_3$Cl, -- therefor.

Signed and Sealed this

Eighth Day of March, 2005

JON W. DUDAS
*Director of the United States Patent and Trademark Office*